United States Patent
Nag et al.

(10) Patent No.: US 10,984,898 B2
(45) Date of Patent: Apr. 20, 2021

(54) COOPERATIVE HEALTH MANAGEMENT SYSTEM

(71) Applicant: Apple Inc., Cupertino, CA (US)

(72) Inventors: Divya Nag, Palo Alto, CA (US); Umer A. Khan, Spring, TX (US)

(73) Assignee: Apple Inc., Cupertino, CA (US)

( * ) Notice: Subject to any disclaimer, the term of this patent is extended or adjusted under 35 U.S.C. 154(b) by 242 days.

(21) Appl. No.: 15/978,126

(22) Filed: May 12, 2018

(65) Prior Publication Data

US 2018/0350453 A1 Dec. 6, 2018

Related U.S. Application Data

(60) Provisional application No. 62/514,214, filed on Jun. 2, 2017.

(51) Int. Cl.
| | |
|---|---|
| G16H 10/60 | (2018.01) |
| G16H 40/63 | (2018.01) |
| G16H 50/30 | (2018.01) |
| G06F 3/0482 | (2013.01) |
| G06F 3/0484 | (2013.01) |
| G06F 3/0488 | (2013.01) |

(52) U.S. Cl.
CPC ........... *G16H 10/60* (2018.01); *G06F 3/0482* (2013.01); *G06F 3/0484* (2013.01); *G16H 40/63* (2018.01); *G16H 50/30* (2018.01); *G06F 3/04883* (2013.01)

(58) Field of Classification Search
CPC .............................................. G06Q 50/22–24
See application file for complete search history.

(56) References Cited

U.S. PATENT DOCUMENTS

| | | | |
|---|---|---|---|
| 7,107,546 B2* | 9/2006 | Coulthard | G06F 3/04895 715/780 |
| 2014/0222446 A1* | 8/2014 | Ash | G06Q 50/22 705/2 |
| 2015/0186602 A1* | 7/2015 | Pipke | G16H 40/67 705/3 |
| 2016/0078778 A1 | 3/2016 | Holland | |

OTHER PUBLICATIONS

International Preliminary Report on Patentability for PCT/US2018/0233303 dated Dec. 3, 2019.

* cited by examiner

*Primary Examiner* — Robert A Sorey
(74) *Attorney, Agent, or Firm* — Dentons US LLP

(57) ABSTRACT

In various implementations, a method includes obtaining first patient display data indicating a first set of health metric types associated with a first patient account and second patient display data indicating a second set of health metric types associated with a second patient account. The method includes receiving, via the network interface, first patient health data associated with the first patient account. The method includes receiving, via the network interface, second patient health data associated with the second patient account. The method includes displaying a user interface including a first patient data region and a second patient data region, the first patient data region including representations of values for the first set of health metric types selected from the first patient health data and the second patient data region including representations of values for the second set of health metric types selected from the second patient health data.

23 Claims, 34 Drawing Sheets

COOPERATIVE HEALTH MANAGEMENT SYSTEM

RELATED APPLICATION

This application claims priority to U.S. Provisional Patent Application No. 62/514,214, filed on Jun. 2, 2017, entitled "Cooperative Health Management System," the entire contents of which are incorporated herein by reference.

TECHNICAL FIELD

The present disclosure relates generally to cooperative health management, and in particular, to user interfaces facilitating cooperative health management.

BACKGROUND

Efficient communication between a patient and one or more health managers, such as doctors, nurses, counselors, physical therapists, etc., can greatly improve the health of the patient. For example, communication regarding currently values of various biometrics of a patient may prompt an action by a health manager. As another example, communication regarding the level of the patient's adherence to a treatment plan may prompt a health manager to urge the patient to increase that level.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

Figure 1:
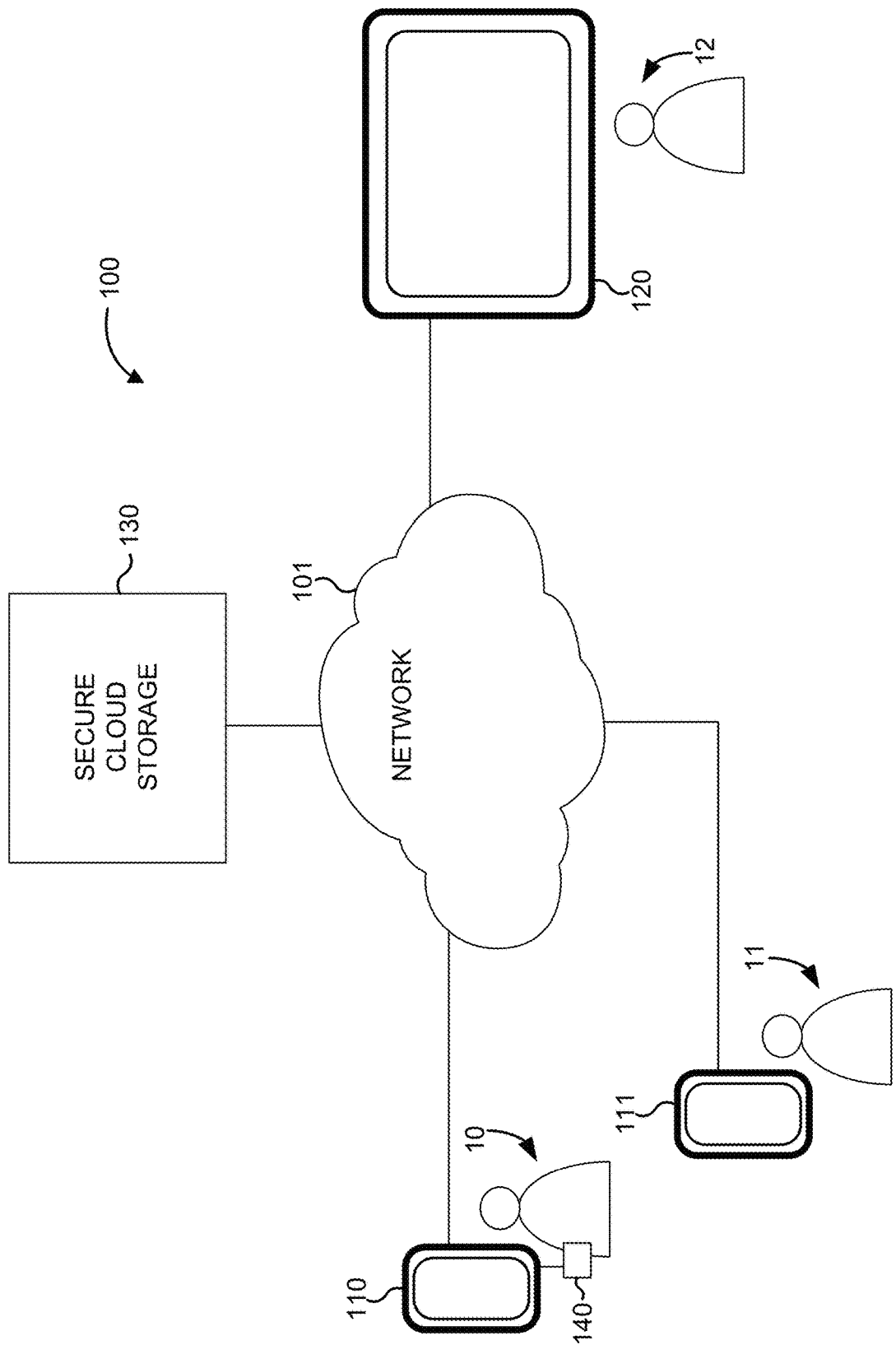
FIG. 1 illustrates a network environment for facilitating collaborative health management in accordance with some implementations.

In accordance with common practice, various features shown in the drawings may not be drawn to scale, as the dimensions of various features may be arbitrarily expanded or reduced for clarity. Moreover, the drawings may not depict all of the aspects and/or variants of a given system, method or apparatus admitted by the specification. Finally, like reference numerals are used to denote like features throughout the figures.

DESCRIPTION OF EXAMPLE EMBODIMENTS

Whereas efficient communication between a patient and one or more health managers can improve the health and/or wellness of the patient, cooperative health management systems can be established in a network environment to facilitate this communication. In various implementations, user devices associated with patients and health managers can execute applications that allow health data and other messages to be securely transmitted between patients and health managers. Further, such applications can provide graphical user interfaces that efficiently present the health data for consumption.

Described herein are methods and system for displaying user interfaces that efficiently convey health data. In various implementations, a user interface is provided at a health manager device that includes patient data regions for a plurality of patients. Each of the patient data regions displays the value of various, custom-chosen-per-patient health metrics. In various implementations, a user interface is provided at a health manager device that displays a relational representation of patient adherence data (e.g., what a patient has done as part of a treatment plan) to patient adherence expectation data (e.g., what a patient is expected to do as part of the treatment plan).

FIG. 1 illustrates a network environment 100 for facilitating collaborative health management in accordance with some implementations. The network environment 100 includes a first patient device 110 associated with a first patient account, logged into by a first patient 10, and further includes a second patient device 111 associated with a second patient account, logged into by a second patient 11. The network environment 100 includes a health manager device 120 associated with a health manager account, logged into by a health manager 12. The first patient device 110, second patient device 111, and health manager device 120 are coupled via a network 101. The network 101 includes any public or private LAN (local area network) and/or WAN (wide area network), such as an intranet, an extranet, a virtual private network, a cable or satellite network, and/or portions of or the entirety of the internet.

Associated with the first patient 10 and communicatively coupled to the first patient device 110 is a biometric device 140. In various implementations, the biometric device 140 is a wearable, such as a smartwatch or fitness watch, a heart rate monitor, a respiratory monitor, a glucose monitor, or a pulse oximeter. The biometric device 140 take biometric measurements of the first patient 10 and provides data indicative of the values of the biometric measurements to the first patient device 110.

Also coupled to the network 101 is a secure cloud storage system 130. The secure cloud storage system 130 can receive and transmit data from the first patient device 110, second patient device 111, and health manager device 120. Data transmitted from the first patient device 110 and the second patient device 120 that is securely stored in the secure cloud storage 130 can be retrieved by the health manager device 120 upon presentation of sufficient credentials. Similarly, data transmitted from the health manager device 120 that is securely stored in the secure cloud storage 130 can be retrieved by either the first patient device 110 or the second patient device 120 upon presentation of sufficient credentials. In various implementations, the secure cloud storage 130 is HIPAA-compliant. In particular, transmission (and storage) of data messages between the various devices is HIPAA-compliant.

The first patient device 110 and the second patient device 120 are configured to present a patient user interface to the first patient 10 and the second patient 11, respectively. Similarly, the health manager device 120 is configured to present a health manager user interface to the health manager 12. Various implementations of the patient user interface and the health manager user interface are described below.

Figure 2A:
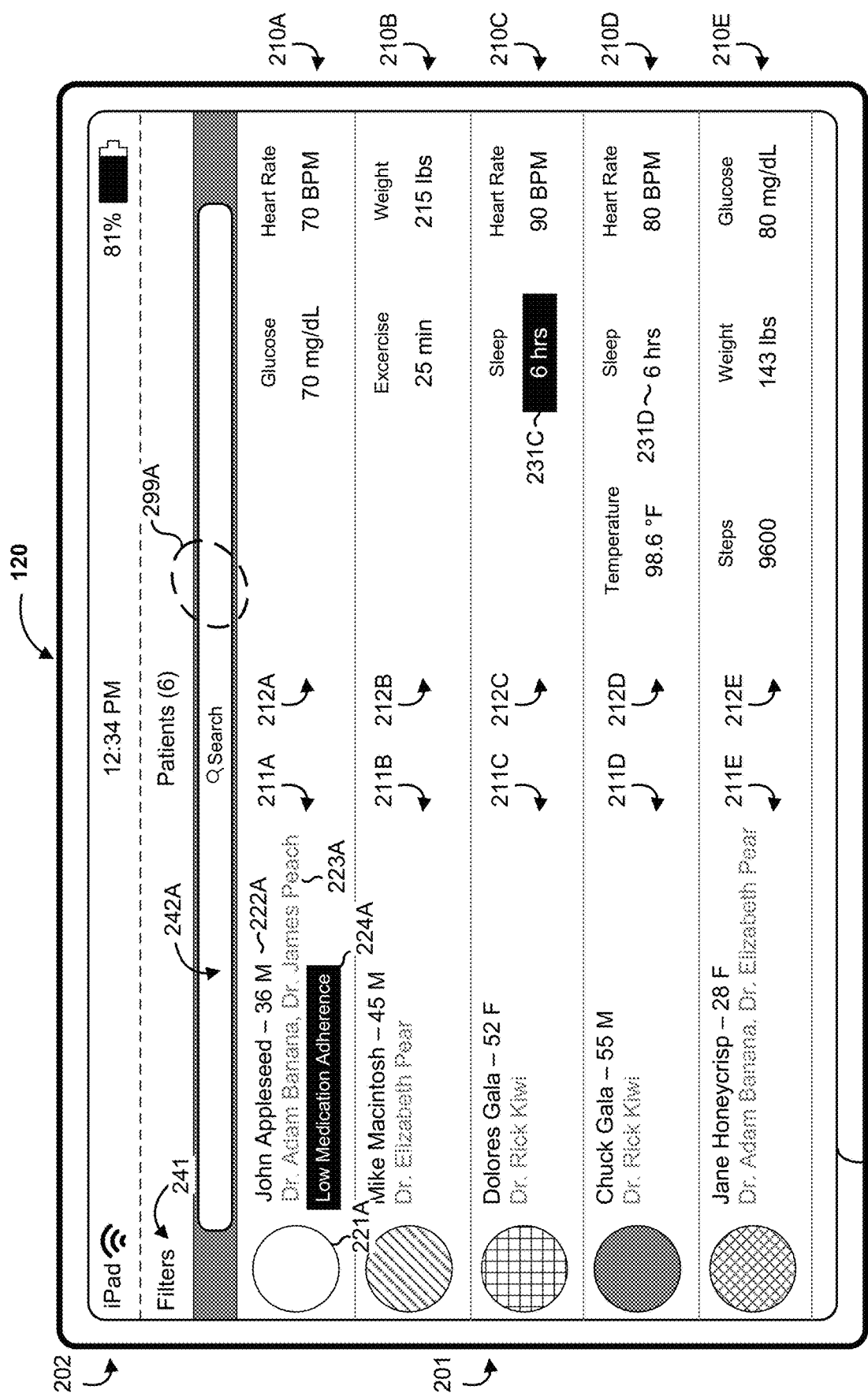
FIGS. 2A-2Z illustrate a health manager user interface in accordance with some implementations.

FIG. 2A illustrates a health manager user interface 200 in accordance with some implementations. FIG. 2A illustrates the health manager user interface 200 including a patient management user interface 201 below a device bar 202. The device bar 202 at the top of the display includes an identifier of the health manager device 120 (e.g., "iPad"), a wireless connection indicator, a current time, and a battery indicator indicating a charge level of the health manager device 120. The health manager user interface 200 includes, below the device bar 202, and spanning the rest of the display, a patient management user interface 201.

The patient management user interface 201 includes a plurality of patient data regions 210A-210E. Each of the patient data regions 210A-210E includes a respective patient identification region 211A-211E and a respective patient health metric region 212A-21E. The patient identification region 211A includes information identifying a patient associated with the patient data region. In various implementations, the patient identification region 211A includes a profile picture 221A and/or other graphical identifier of the patient, a name 222A and/or other textual identifier of the patient (including, for example, an age and/or gender of the patient), and treating health managers of the patient 223A. In various circumstances, the patient identification region 211A includes an alert indication 224A that data associated with patient has exceeded a threshold, e.g., is less than or greater than a prescribed value.

The patient health metric region 212A includes representations of values of various health metric types of the patient (each representation referred to herein as a "health widget"). In various implementations, the various health metric types are different for different patients (e.g., are different in different patient data regions 210A-210E). In various implementations, the health metric types are customizable and can be set by a health manager as described further below. Accordingly, the health metric types in a first patient health metric region 212A are different than the health metric types in a second patient health metric region 212B.

In various circumstances, the value for a health metric type exceeds an alert threshold. For example, for a third patient associated with a third patient data region 210C, the value of the sleep metric type exceeds a threshold (e.g., is less than a prescribed value), and the health widget 231C is displayed in a different manner than other health widgets. For example, in various implementations, the health widget 231C is displayed in a different color, a different font, a different size, a different background color (highlighting), or with any other visual alert indication. In various implementations, the threshold for the same health metric type is different for different patients. Thus, the health widget 231D is displayed in the same manner as the other widgets.

The patient management user interface 201 includes a filter menu affordance 241 for selecting one or more filter criteria and a search bar 242A for inputting a search query.

FIG. 2A illustrates a contact 299A detected at a location of the search bar 242A. In various implementations, the contact 299A (and other contacts described herein) is a finger touch at the location of the health manager user interface 200 displayed on a touch-sensitive display. In various implementations, the contact 299A (and other contacts described herein) is a stylus contact at the location of the health manager user interface 200 displayed on a touch-sensitive display. In various implementations, the contact 299A (and other contacts described herein) is a mouse-click when a cursor is at the location of the health manager user interface 200. In various implementations, the contact 299A (and other contacts described herein) is a touchpad (a touch-sensitive device separate from the display) touched or pressed when a cursor is at the location of the health manager user interface 200.

Figure 2B:
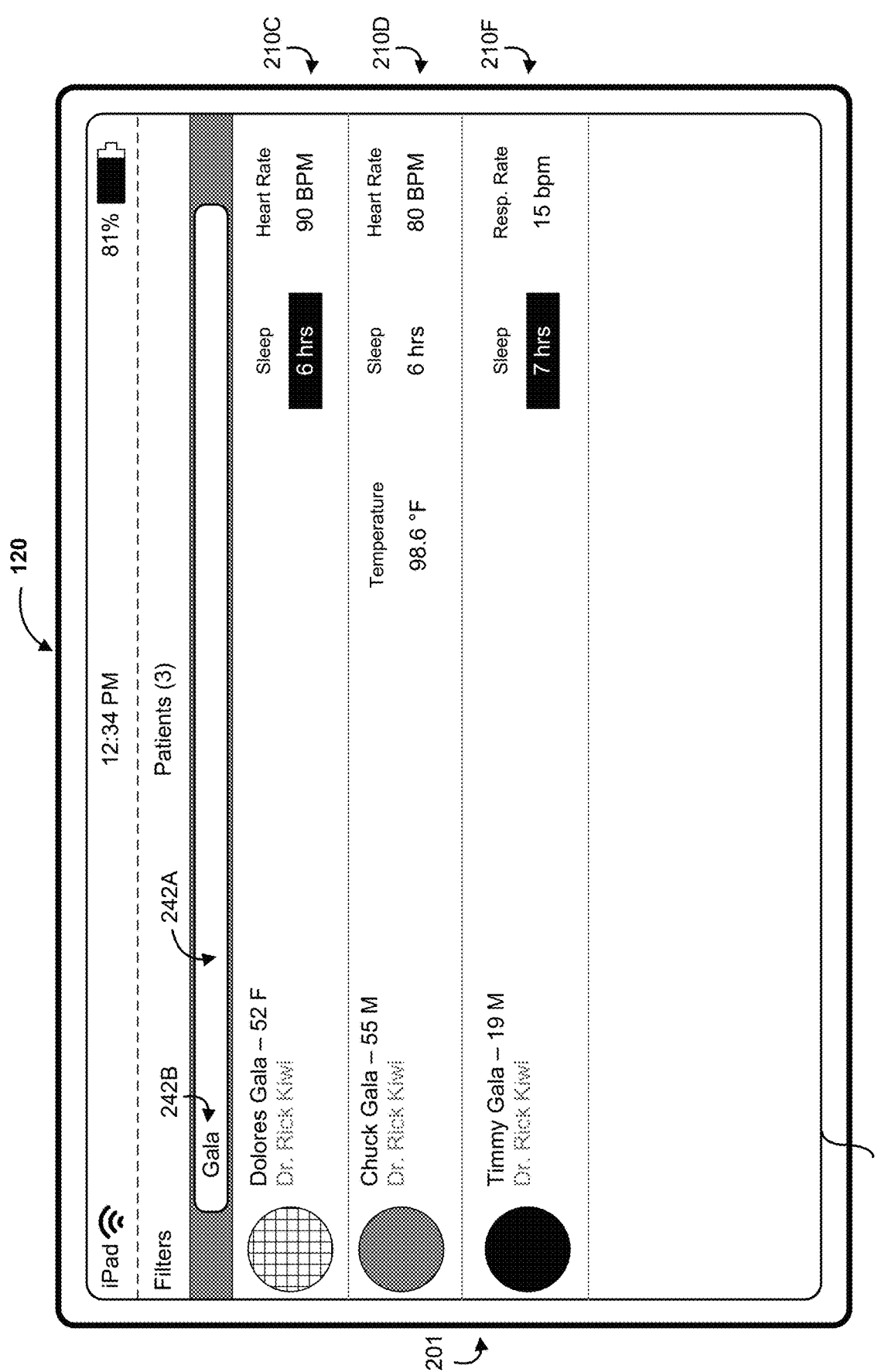

FIG. 2B illustrates the health manager user interface 200 of FIG. 2A in response to detecting the contact 299A at the location of the search bar 242A and input of a search query 242B. In FIG. 2B, the patient manager user interface 201 includes patient data regions 210C, 210D, and 210F having associated data that matches the search query. Although FIG. 2B illustrates that each of the patient data regions 210C, 210D, and 210F have patient name data that at least partially matches the search query, in various implementations, the patient data regions can have other data (such as treating health manager data or patient categorization data) that at least partially matches the search query.

Figure 2C:
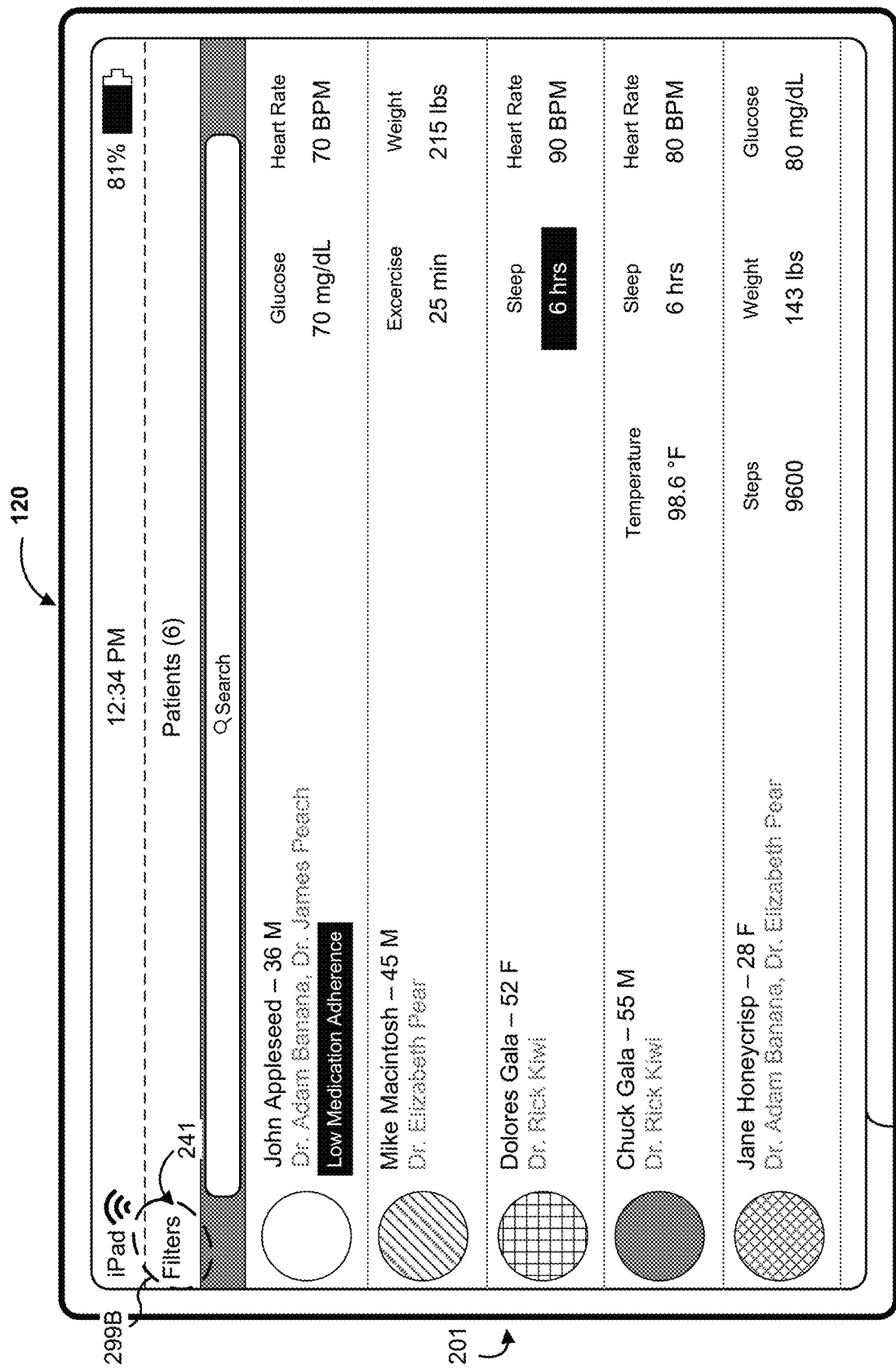

FIG. 2C illustrates the health manager user interface 200 of FIG. 2A with a contact 299B detected at a location of the filter menu affordance 241 of the patient management user interface 201.

Figure 2D:
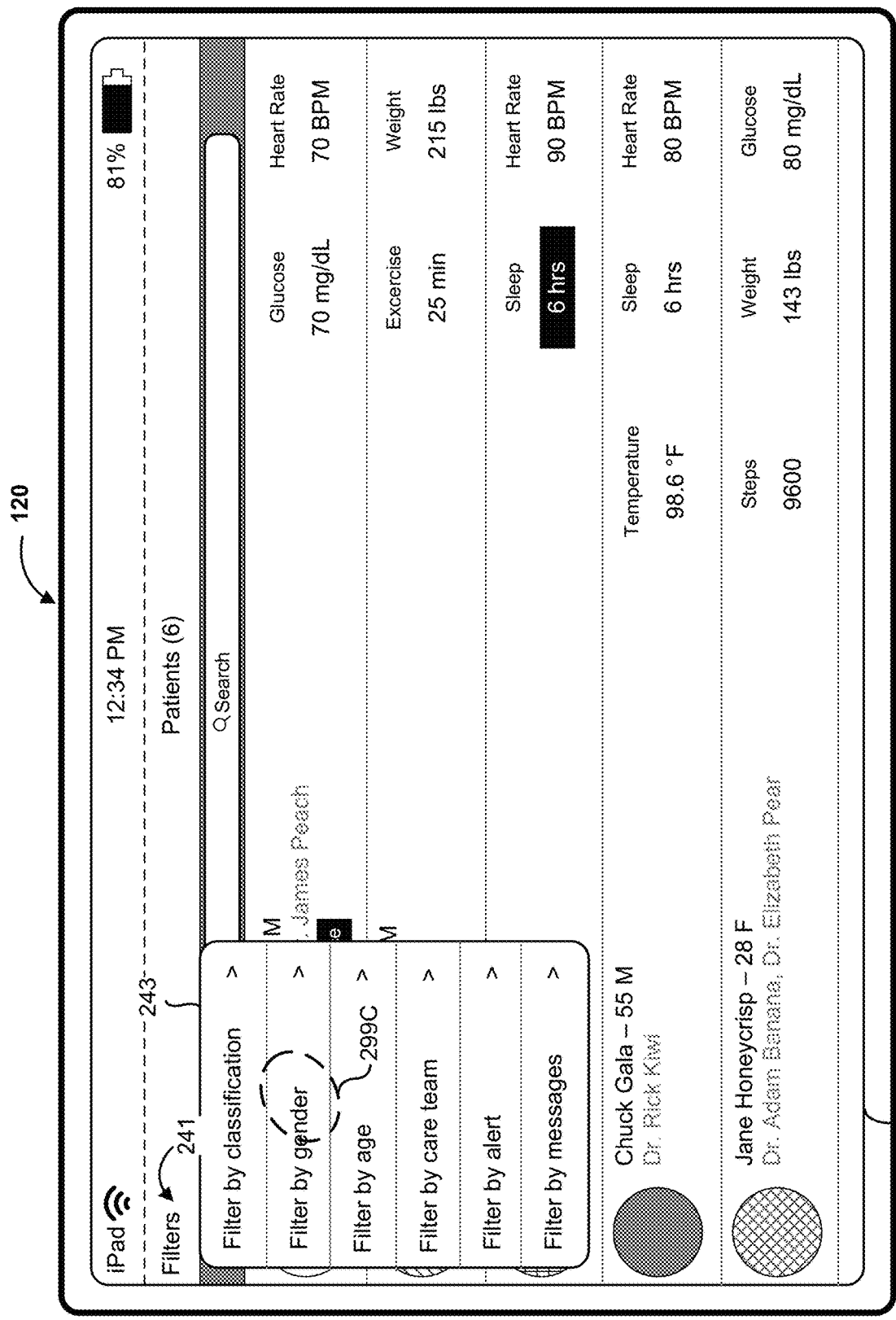

FIG. 2D illustrates the health manager user interface 200 of FIG. 2C in response to detecting the contact 299B at the location of the filter menu affordance 241. In response to detecting the contact 299B at the location of the filter menu affordance 241, a filter criteria menu 243 is displayed. The filter criteria menu 243 includes options to select one or more filter criteria. In various implementations, the options include an option to filter by patient category. Each patient may be assigned one or more categories (e.g., diabetic, weight loss, prenatal, insomnia, etc.) and data indicative of the category can be stored in association with the patient account. In various implementations, the options include an option to filter by gender and an option to filter by age. In various implementations, the options include an option to filter by treating health managers of the patient. In various implementations, the options include an option to filter by the presence (or absence) of alerts or messages. FIG. 2D illustrates a contact 299C detected at a location of the option to filter by gender.

Figure 2E:
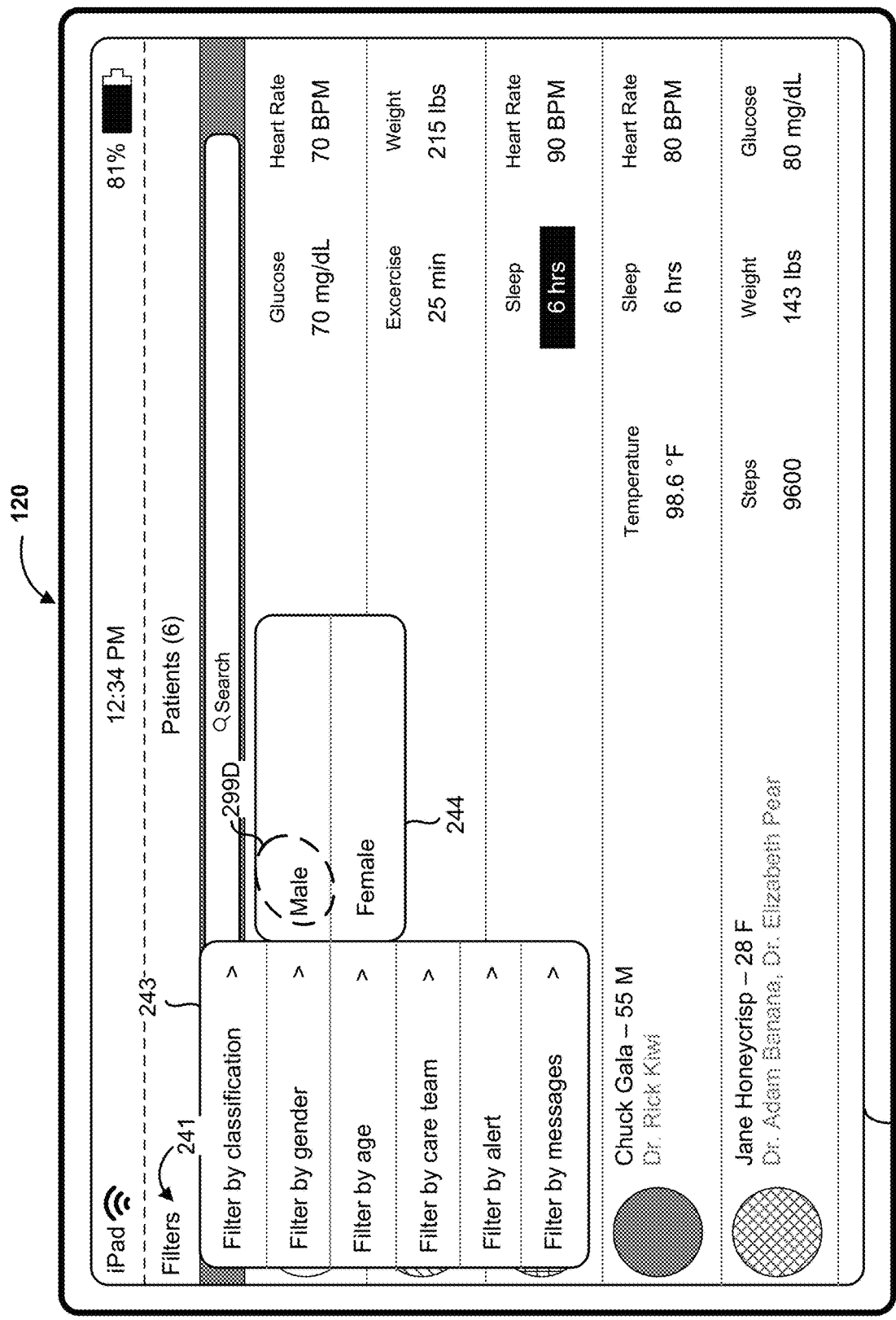

FIG. 2E illustrates the health manager user interface 200 of FIG. 2D in response to detecting the contact 299C at the location of the option to filter by gender. In FIG. 2E, a filter criteria selection menu 244 is displayed with options to specify details regarding filter criteria. In FIG. 2E, the filter criteria selection menu 244 includes an option to filter by gender to display patient data regions associated with male patients and an option to filter by gender to display patient data regions associated with female patients. FIG. 2E illustrates a contact 299D detected at a location of the option to filter by gender to display patient data regions associated with male patients.

Figure 2F:
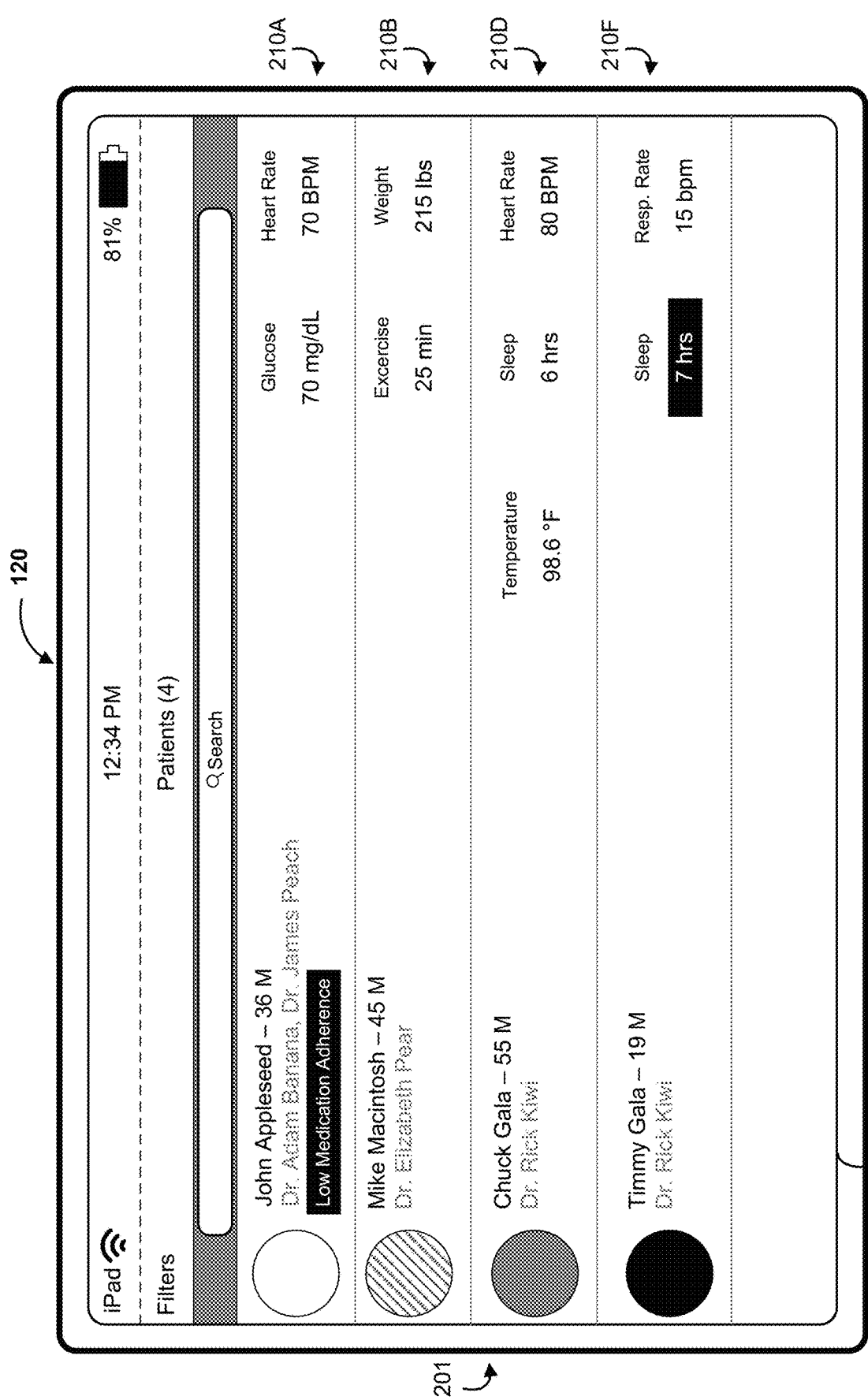

FIG. 2F illustrates the health manager user interface 200 of FIG. 2E in response to detecting the contact 299D at the location of the option to filter by gender to display patient data regions associated with male patients. In FIG. 2E, the patient manager user interface 201 includes patient data regions 210A, 210B, 210D, and 210F having associated data that matches the filter criteria, e.g., patient data regions associated with male patients.

Figure 2G:
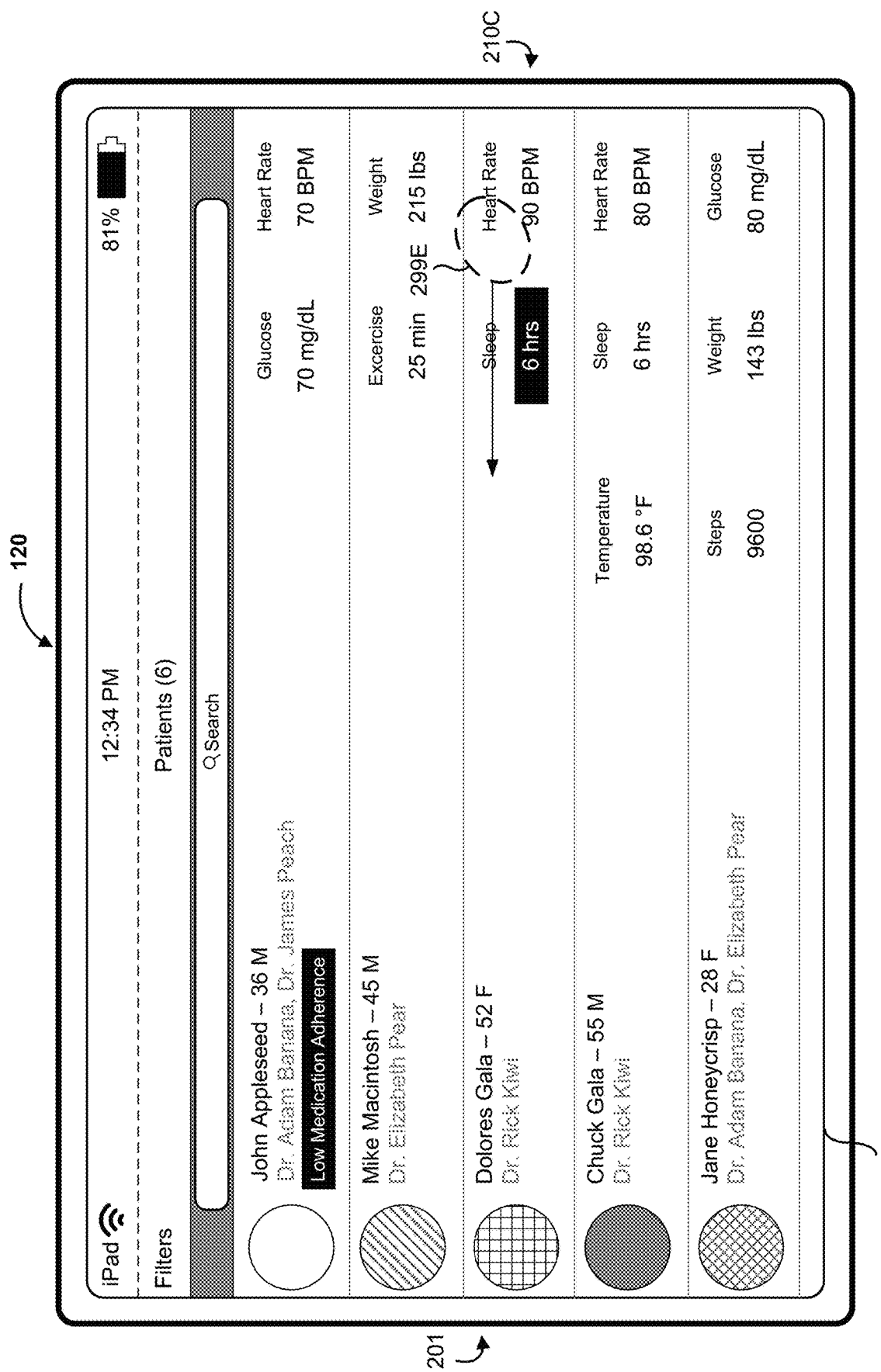

FIG. 2G illustrates the health manager user interface 200 of FIG. 2A with movement of a contact 299E detected within the third patient data region 210E.

Figure 2H:
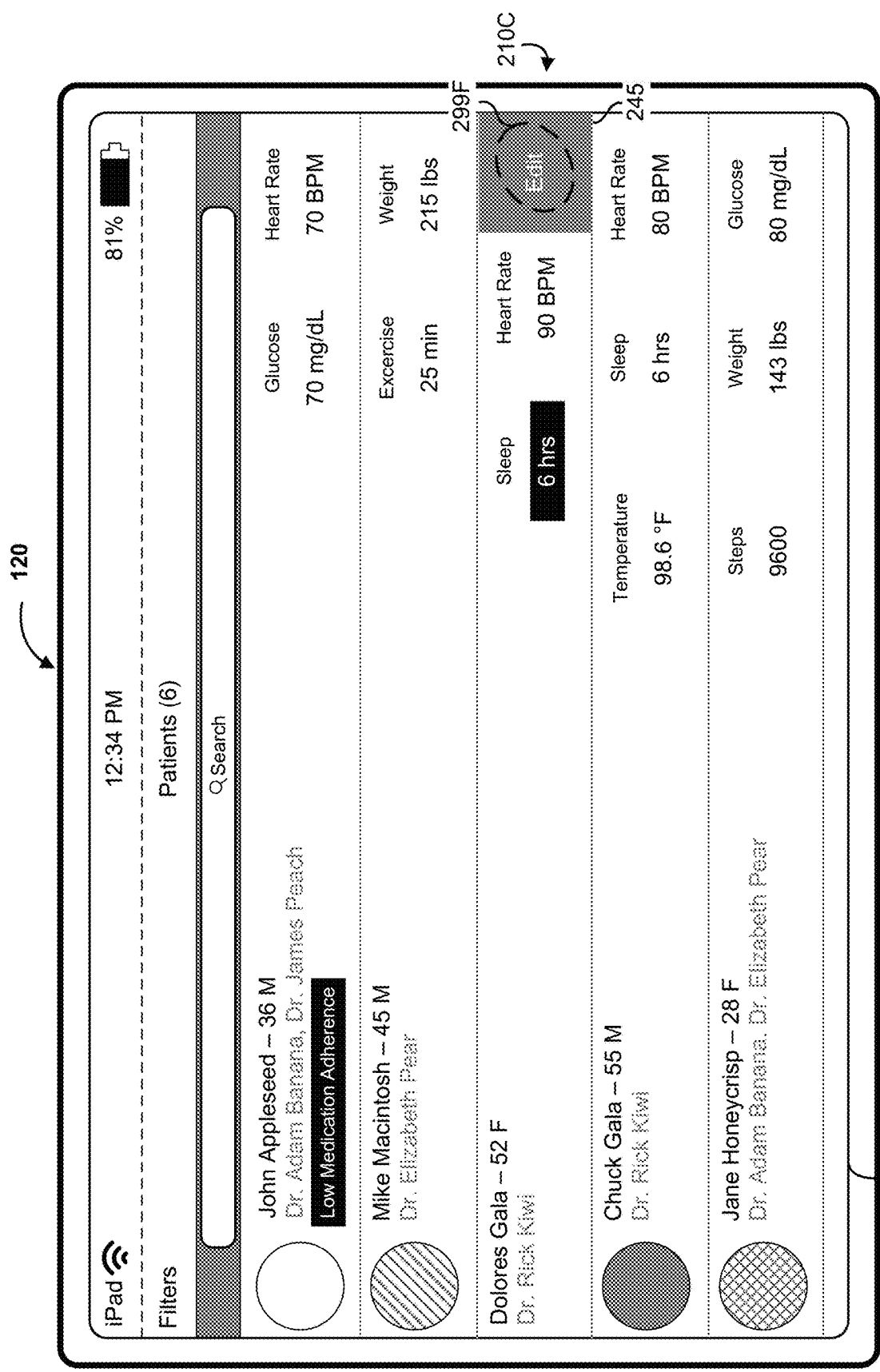

FIG. 2H illustrates the health manager user interface 200 of FIG. 2G in response to detecting movement of the contact 299E within the third patient data region 210E. In FIG. 2H, the third patient data region 210C is shifted to reveal a health widget edit affordance 245. FIG. 2H illustrates a contact 299F detected at a location of the health widget edit affordance 245.

Figure 2I:
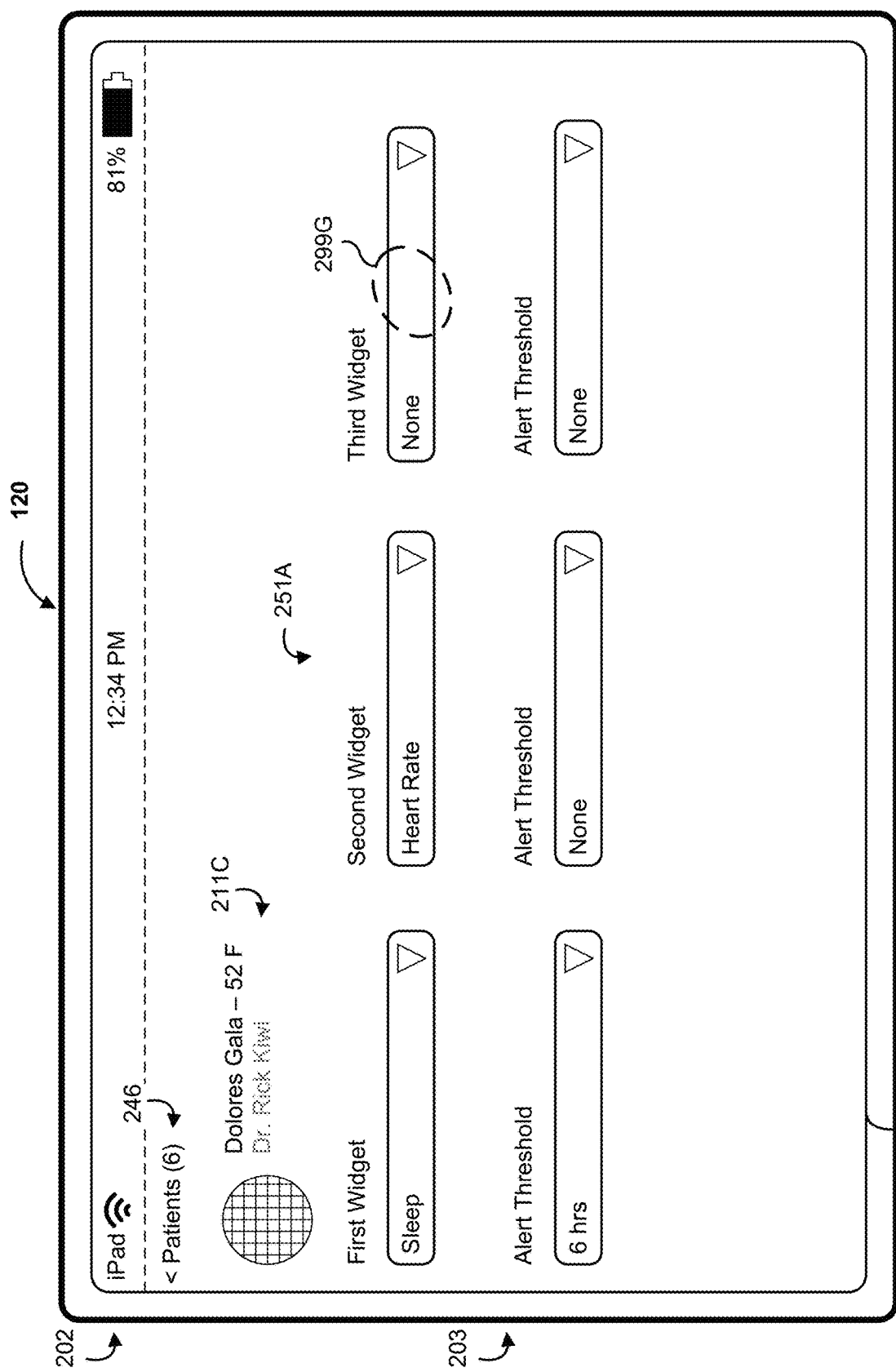

FIG. 2I illustrates the health manager user interface 200 of FIG. 2H in response to detecting the contact 299F at the location of the health widget edit affordance 245. In FIG. 2I, the health manager user interface 200 includes, below the device bar 202, a widget edit user interface 203. The widget edit user interface 203 allows a health manager to change the health metric types displayed in the patient health metric region 212C of the patient data region 210C. Although FIGS. 2G-2I illustrates one method of reaching the widget edit user interface 203, various implementations employ other methods of reaching the widget edit user interface 203 or otherwise changing the health metric types displayed in the patient health metric regions of the patient data regions.

The widget edit user interface 203 includes a return affordance 246 for returning to the patient management user interface 201. The widget edit user interface 203 also includes the patient identification region 211C for the selected patient. The widget edit user interface 203 includes a widget data edit region 251A including various options for selecting various health metric types to be displayed in the patient health metric region 212C and for selecting alert thresholds associated with the various health metric types. FIG. 2I illustrates a contact 299G detected at a location of an option to change a third health metric type.

Figure 2J:
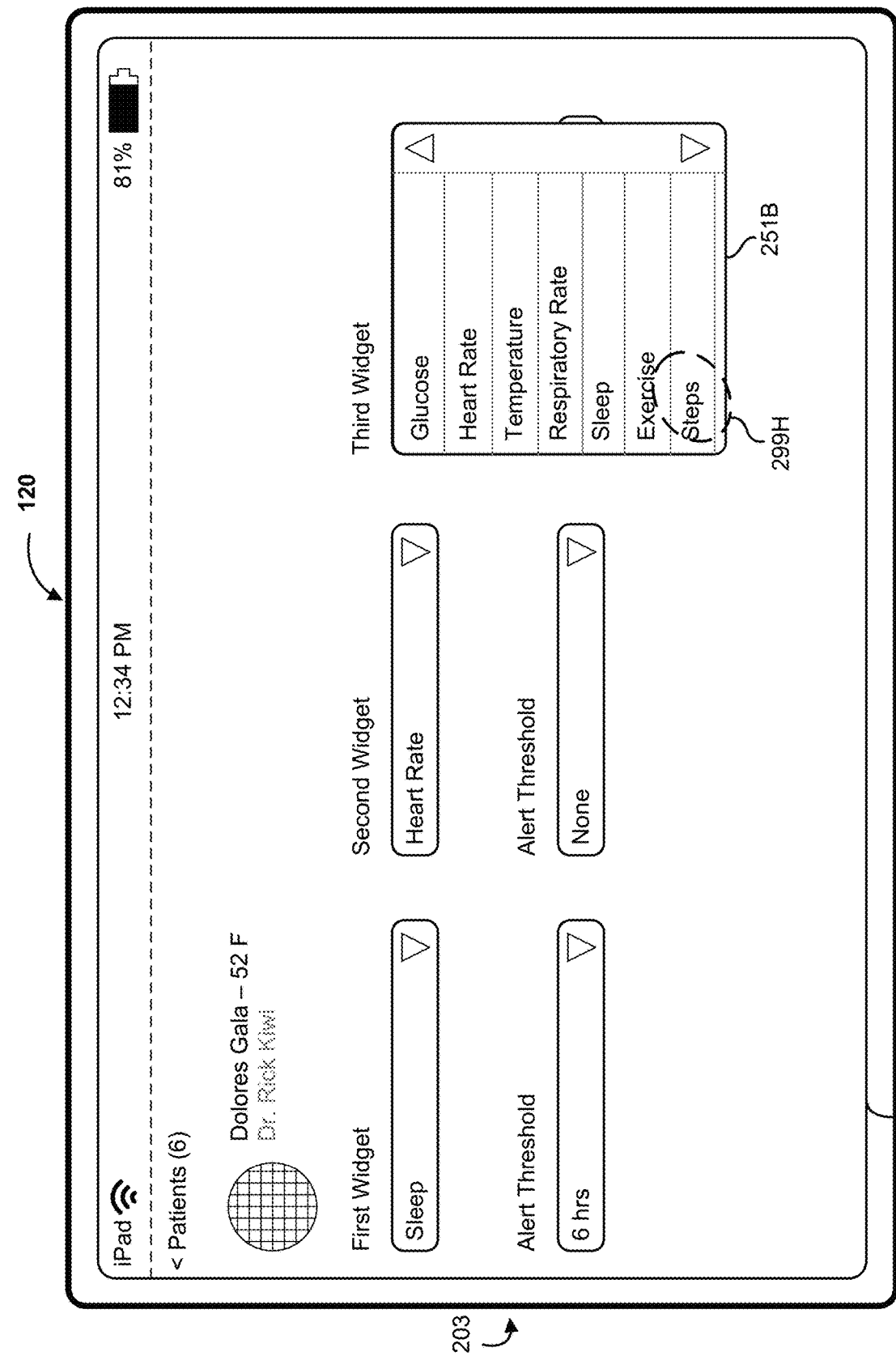

FIG. 2J illustrates the health manager user interface 200 of FIG. 2I in response to detecting the contact 299G at the location of the option to change the third health metric type. In FIG. 2J, the option to change the third health metric type is expanded into a dropdown menu 251B listing a variety of health metric types that can be displayed as a health widget. In various implementations, the listing of health metric types is sorted in health metric type categories (e.g., health metric types for weight loss, health metric types for diabetes, health metric types for insomnia, etc.). In various implementations, the listing of health metric types is searchable by user input of a search query. FIG. 2J illustrates a contact 299H at the location of an option to change the third health metric type to a steps metric.

Figure 2K:
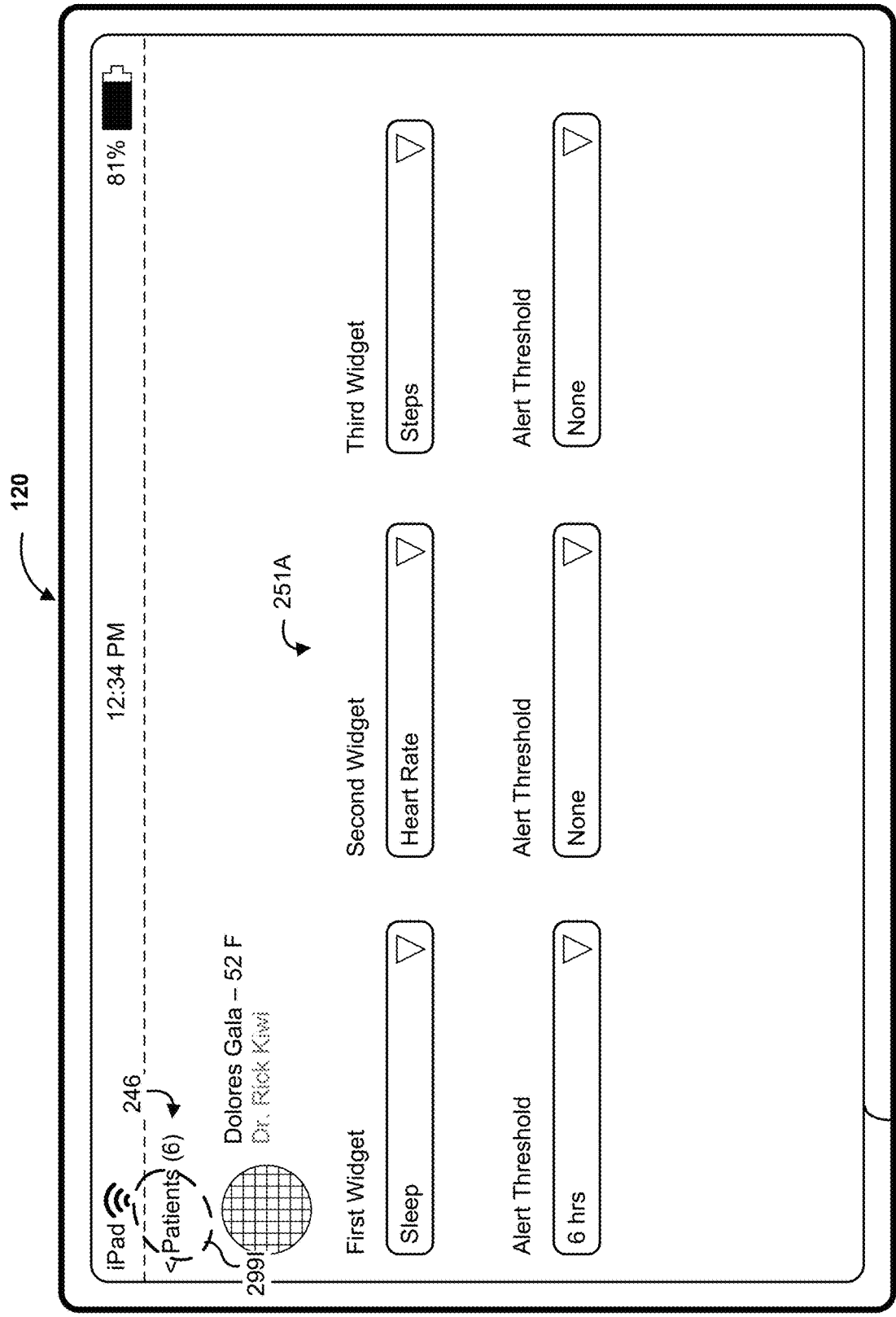

FIG. 2K illustrates the health manager user interface 200 of FIG. 2J in response to detecting the contact 299H at the location of the option to change the third health metric type to a steps metric. In FIG. 2K, the widget data edit region 251A indicates that the third health metric type has been set to a steps metric. FIG. 2K illustrates a contact 299I detected at a location of the return affordance 246.

Figure 2L:
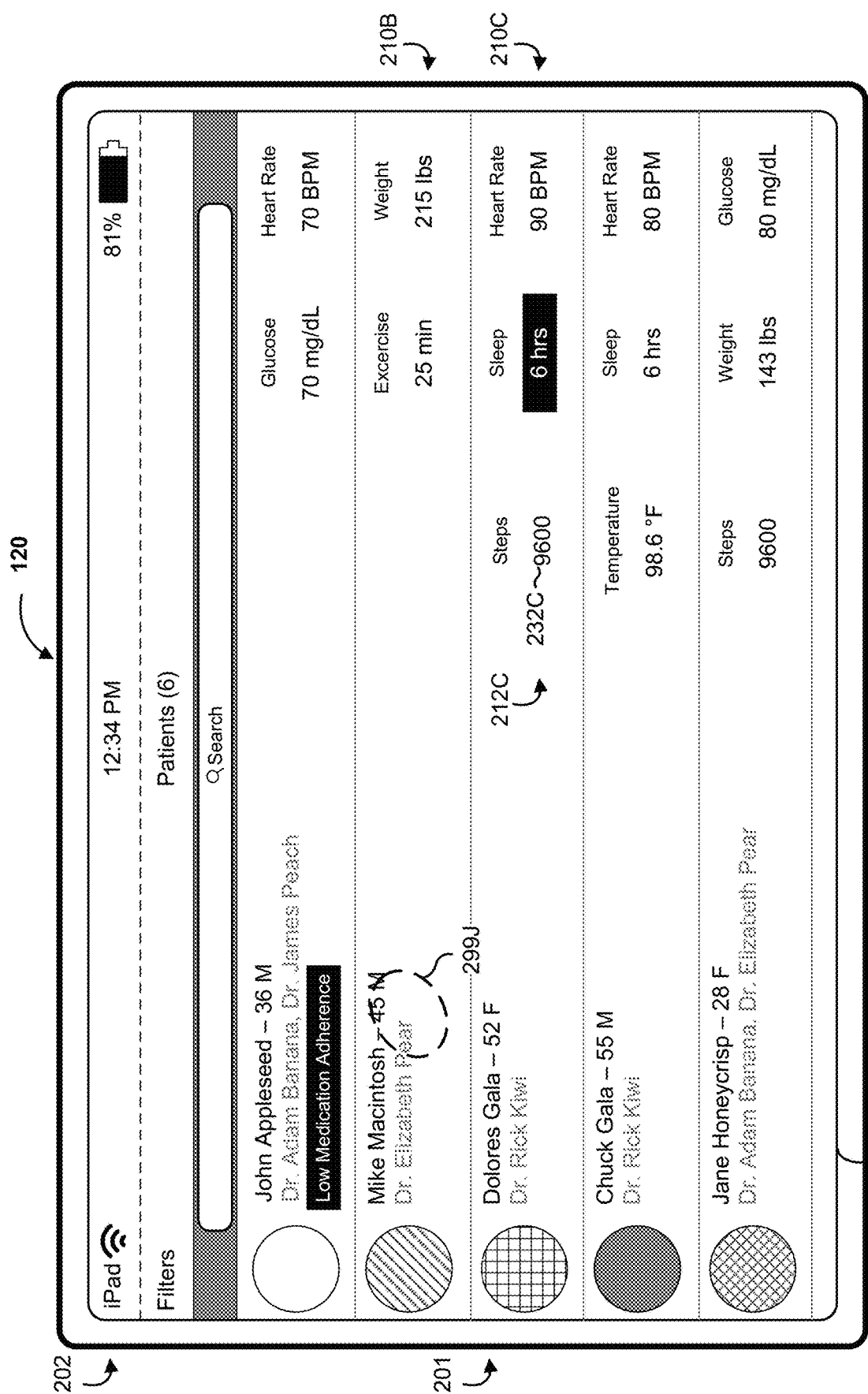

FIG. 2L illustrates the health manager user interface 200 of FIG. 2K in response to detecting the contact 299I at the location of the return affordance 246. In response to detecting the contact 299I at the location of the return affordance 246, the widget edit user interface 203 is replaced with the patient management user interface 201. In response to the interaction with the widget edit user interface 203, the patient health metric region 212C of the patient data region 210C includes a third widget 232C including a representation of a value indicative of number of steps taken by the patient. FIG. 2L illustrates a contact 299J detected at a location of a second patient data region 210B.

Figure 2M:
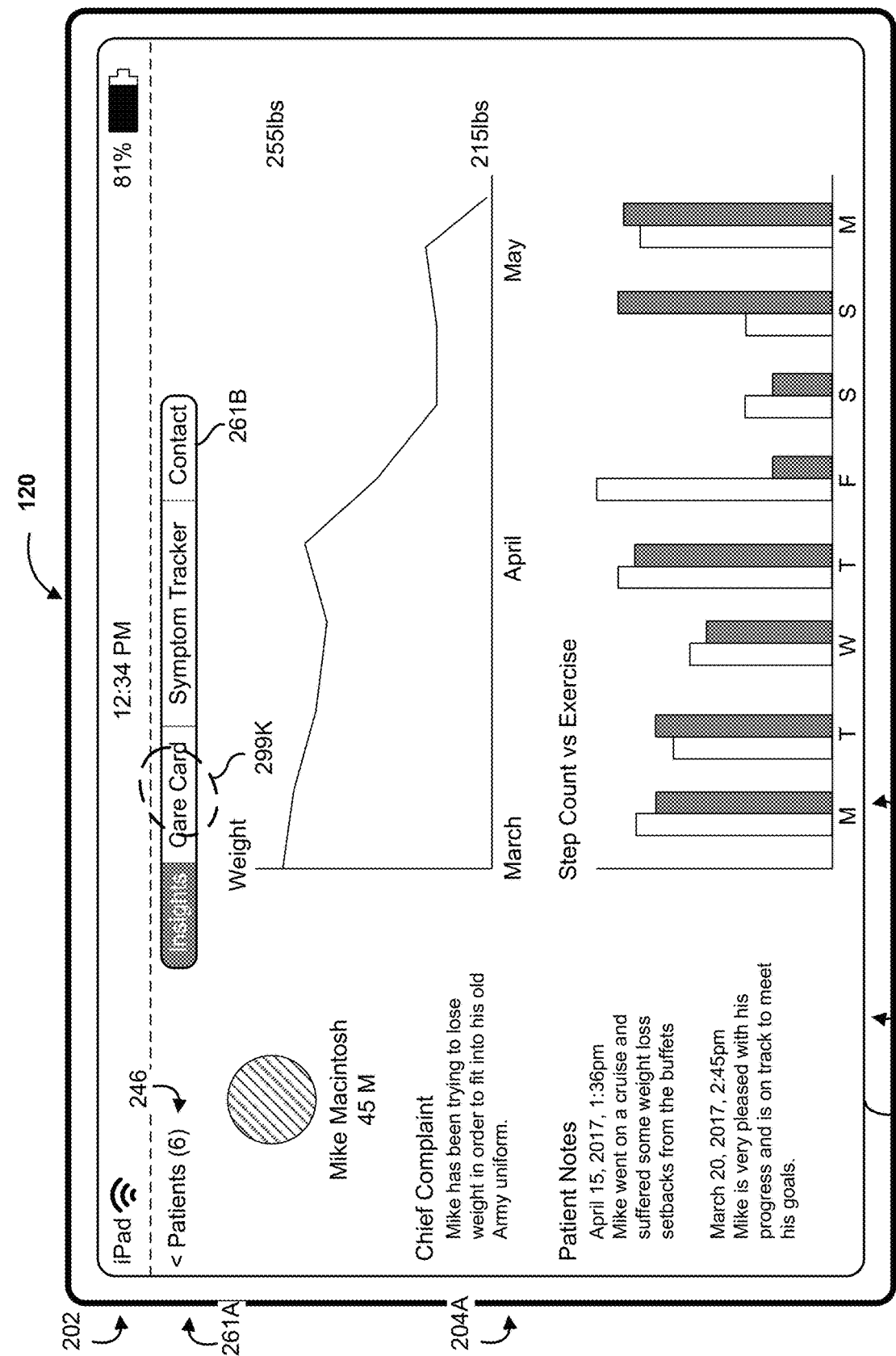

FIG. 2M illustrates the health manager user interface 200 of FIG. 2L in response to detecting the contact 299J at the location of the second patient data region 210B. In FIG. 2M, the health manager user interface 200 includes, below the device bar 202, an insights user interface 204A. The insights user interface 204A includes a user interface switch bar 261A that includes the return affordance 246 and a user interface switch affordance 261B for switching between the insights user interface 204A, a care card user interface 204B, a symptom tracker user interface 204C, and a contact user interface 204D.

The insights user interface 204A includes a patient history region 261C and a patient graph region 261D. The patient history region 261C includes patient identifying information (such as a profile picture, a name, age, gender, and chief complaint). In various implementations, which patient identifying information is displayed in the patient history region 261C is customizable. In various implementations, the patient history region 261C includes timestamped patient notes. The patient graph region 261D includes graphs of values of health metrics associated with the patient. In various implementations, the graphs are automatically selected based on the health data available. In various implementations, which graphs are displayed in the patient graph region 261D is customizable. FIG. 2M illustrates a contact 299K detected at a location of the user interface switch affordance 261B to switch to the care card user interface 204B.

Figure 2N:
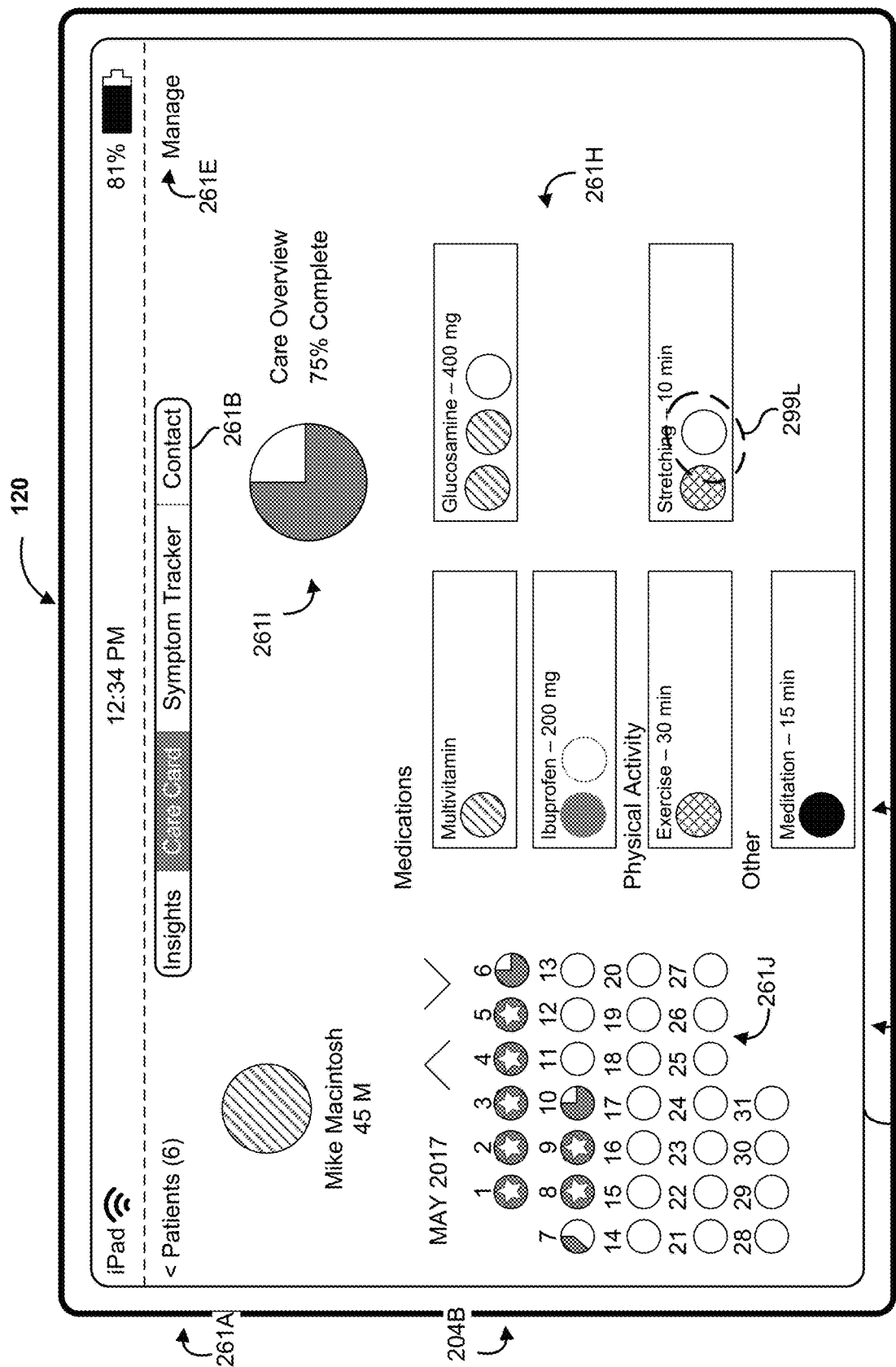

FIG. 2N illustrates the health manager user interface 200 of FIG. 2M in response to detecting the contact 299K at the location of the user interface switch affordance 261B to switch to the care card user interface 204B. In FIG. 2N, the insights user interface 204A is replaced with the care card user interface 204B. The care card user interface 204B includes the user interface switch bar 261A. In the care card user interface 204B, the user interface switch bar 261A includes a manage affordance 261E for switching to a care card management user interface 204E, described further below.

The care card user interface 204B includes a historical activity adherence region 261F and a daily activity adherence region 261G. The daily activity adherence region 261G includes a plurality of activity indicia 261H corresponding to activities the patient is expected to complete on a particular date, e.g., as part of a treatment plan. In various implementations, the activity indicia 261H further include optional activity indicia corresponding to optional activities the patient may complete, but are not expected to complete, such as taking an ibuprofen pill for pain as needed.

In some circumstances, a patient is expected to complete a particular activity multiple times on a particular date. Thus, in various implementations, the plurality of activity indicia 261H include a plurality of activity indicia 261H associated with the same activity (e.g., in FIG. 2N, there are three activity indicia 261H associated with taking a glucosamine pill). In various implementations, the activity indicia 261H are organized into sets (e.g., by activity and/or activity type (e.g., medications, physical activity, and other)). In various implementations, activity indicia 261H associated with one set are displayed in a different manner than activity indicia 261H associated with another set. For example, in FIG. 2N, the activity indicia 261H associated with taking a multivitamin is displayed in a different color than the activity indicia 261H associated with performing meditation. In various implementations, different sets of activity indicia 261H are displayed in a different color, size, shape, or font.

In various implementations, activity indicia 261H associated with activities that the patient has completed are displayed in a different manner than activity indicia 261H associated with activities that the patient has yet to complete. For example, the first two activity indicia 261H associated with taking a glucosamine pill are displayed as filled shapes and the last activity indicia 261H associated with taking a glucosamine pill is displayed as an unfilled shape. In various implementations, activity indicia 261H associated with completed activities are displayed in a different color, size, shape or font than activity indicia 261H associated with uncompleted activities. In various implementations, the first manner includes a completion indicator and the second manner does not include the completion indicator. In various implementations, the completion indicator is a shape fill. Thus, activity indicia 261H associated with completed activities include a filled shape and activity indicia 261H associated with uncompleted activities include an unfilled shape. In some embodiments, the completion indicator is a checkmark within the activity indicia 261H. In some embodiments, the completion indicator is a value within the activity indicia 261H (e.g., a time of day the activity was completed).

The daily activity adherence region 261G includes a daily percentage indicator 261I that indicates the percentage of activities the patient is expected to complete on a particular date that the patient has actually completed. In various implementations, the daily percentage indicator 261I includes a textual and/or a graphical indicator.

The historical activity adherence region 261F includes patient identifying information (such as a profile picture, a name, age, and gender). The historical activity adherence region 261F includes an activity adherence calendar 261J including daily percentage indicators for a variety of dates (e.g., for each date in a particular month). In various implementations, daily percentage indicators of the calendar (and, optionally, the daily percentage indicator 261I in the daily activity adherence region 261G) that are 100% complete (or at least greater than a predefined threshold) are displayed with a completion indicator, such as a star or a checkmark.

FIG. 2N illustrates a contact 299L detected at a location of an activity indicia 261H associated with stretching.

Figure 2O:
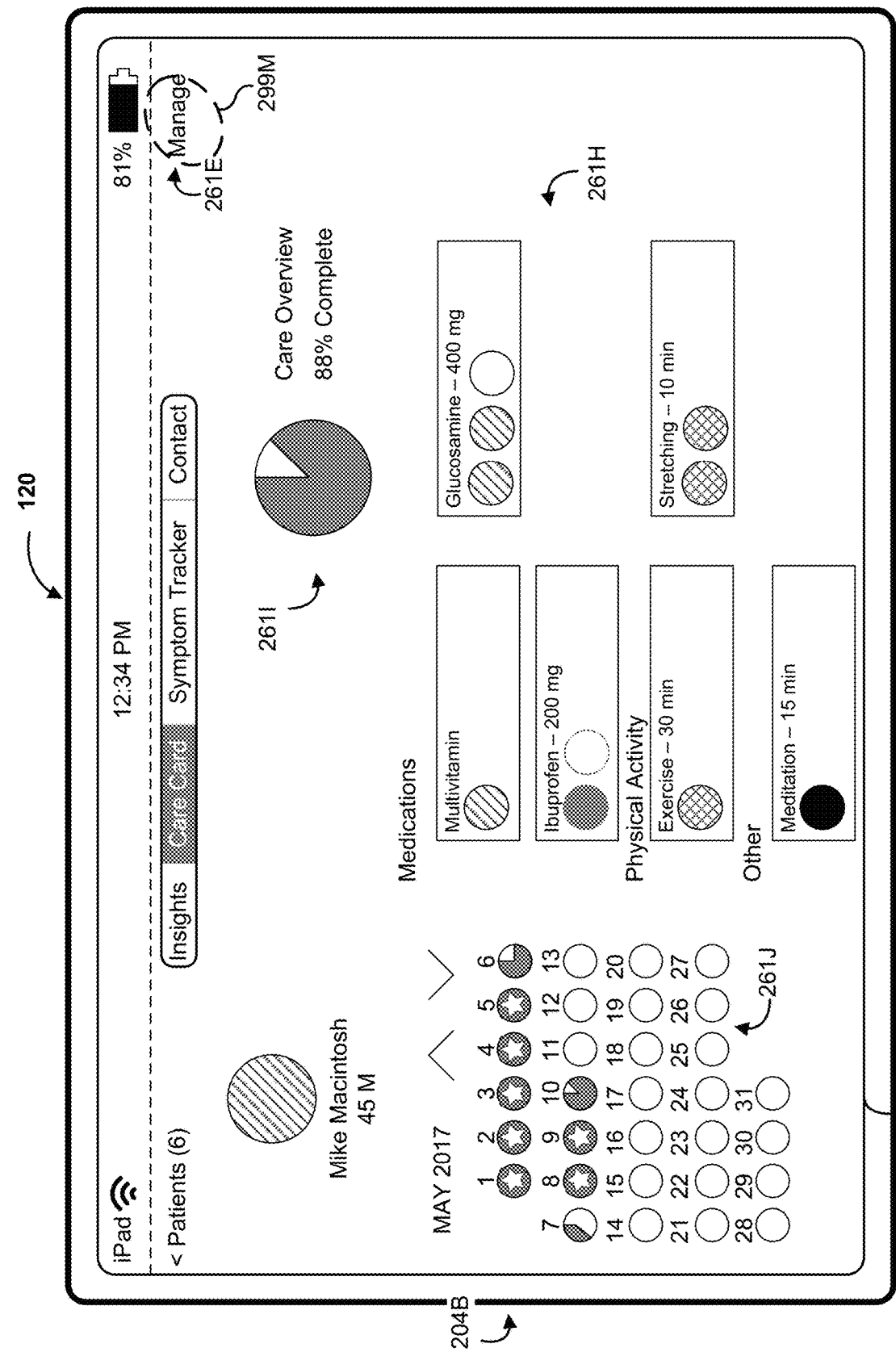

FIG. 2O illustrates the health manager user interface 200 of FIG. 2N in response to detecting the contact 299L at the location of the activity indicia 261H associated with stretching. In FIG. 2O, the activity indicia 261H associated with stretching is displayed in a different manner to indicate that the activity has been completed. Further, the daily percentage indicator 261I has increased (as also reflected on the same date in the activity adherence calendar 261J). FIG. 2O illustrates a contact 299M at a location of the manage affordance 261E.

Figure 2P:
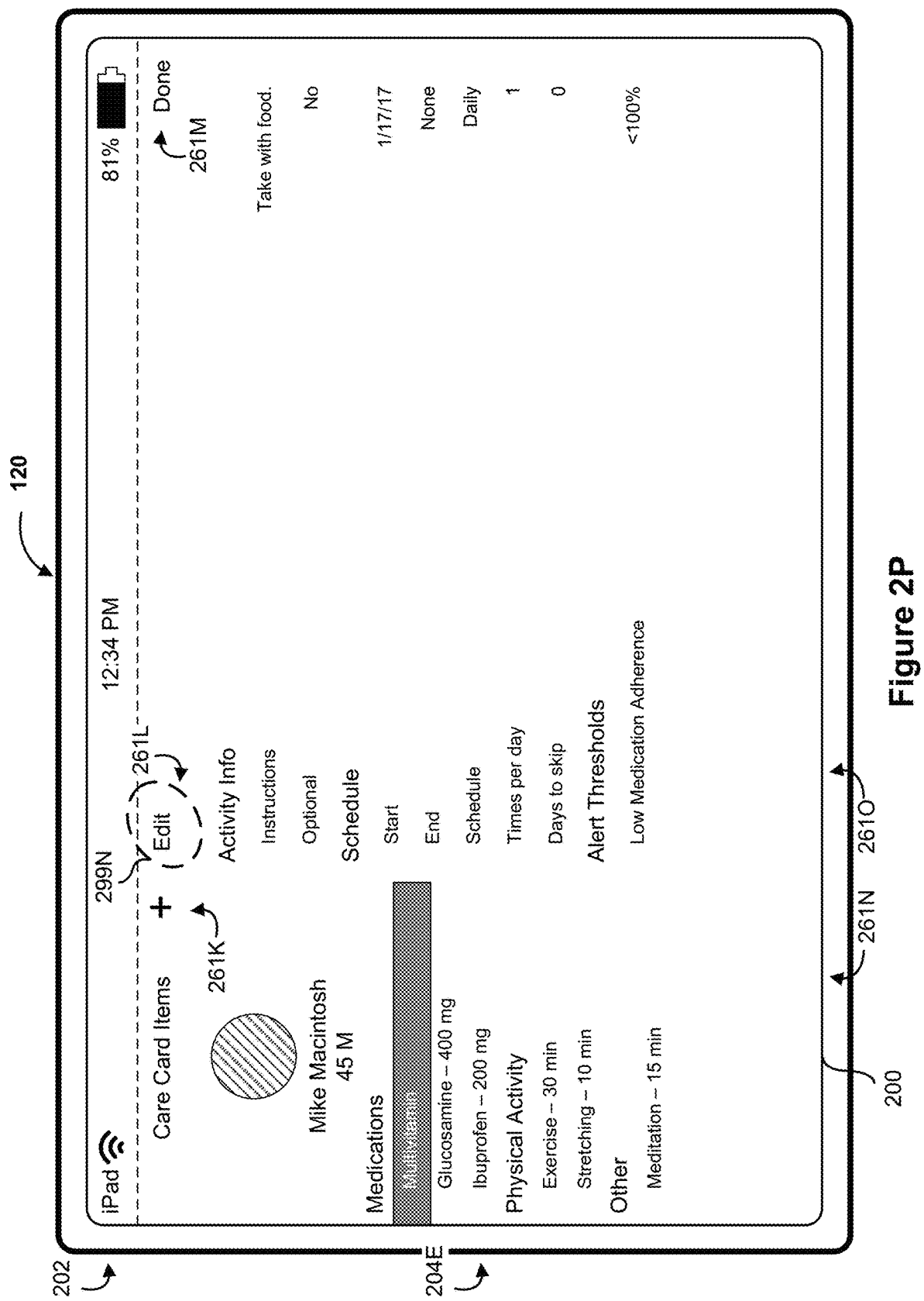

FIG. 2P illustrates the health manager user interface 200 of FIG. 2O in response to detecting the contact 299M at the location of the manage affordance 261E. In FIG. 2P, the health manager user interface 200 includes, beneath the device bar 202, the care card management user interface 204E. The care card management user interface 204E includes an activity listing region 261N that includes patient identifying information and an activity listing. The activity listing includes an entry for each activity the patient is expected to complete, regardless of date. The care card management user interface 204E includes an activity details region 261O that includes details regarding an activity selected from the activity listing. In various implementations, the activity details include an indication of whether the activity is optional or not. In various implementations, the activity details include a schedule at which the activity is expected to be performed. In various implementations, the activity details include a threshold at which an alert is generated for the activity.

The care card management user interface 204E includes an add item affordance 261K for adding one or more activities to the activity listing, an edit item affordance 261L for editing the details of the activity selected from the activity listing, and a return affordance 261M for returning to the care card user interface 204B. FIG. 2P illustrates a contact 299N detected at a location of the edit item affordance 261L.

Figure 2Q:
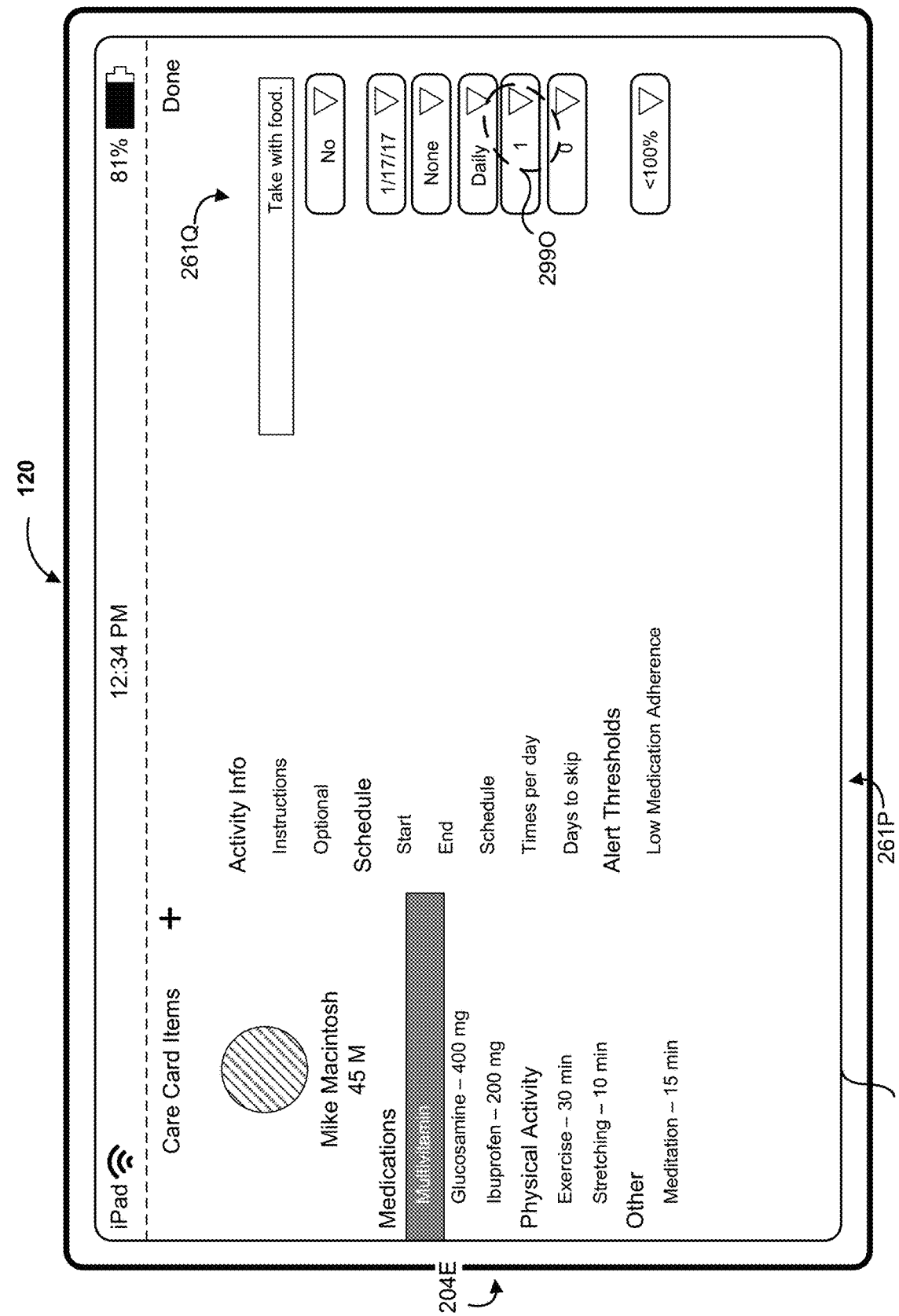

FIG. 2Q illustrates the health manager user interface 200 of FIG. 2P in response to detecting the contact 299N at the location of the edit item affordance 261L. In FIG. 2Q, the activity details region 261O is replaced with an activity details edit region 261P including a number of options 261Q for changing the details of the selected activity. FIG. 2Q illustrates a contact 299O at a location of an option for changing the number of times a day an activity is expected to be completed.

Figure 2R:
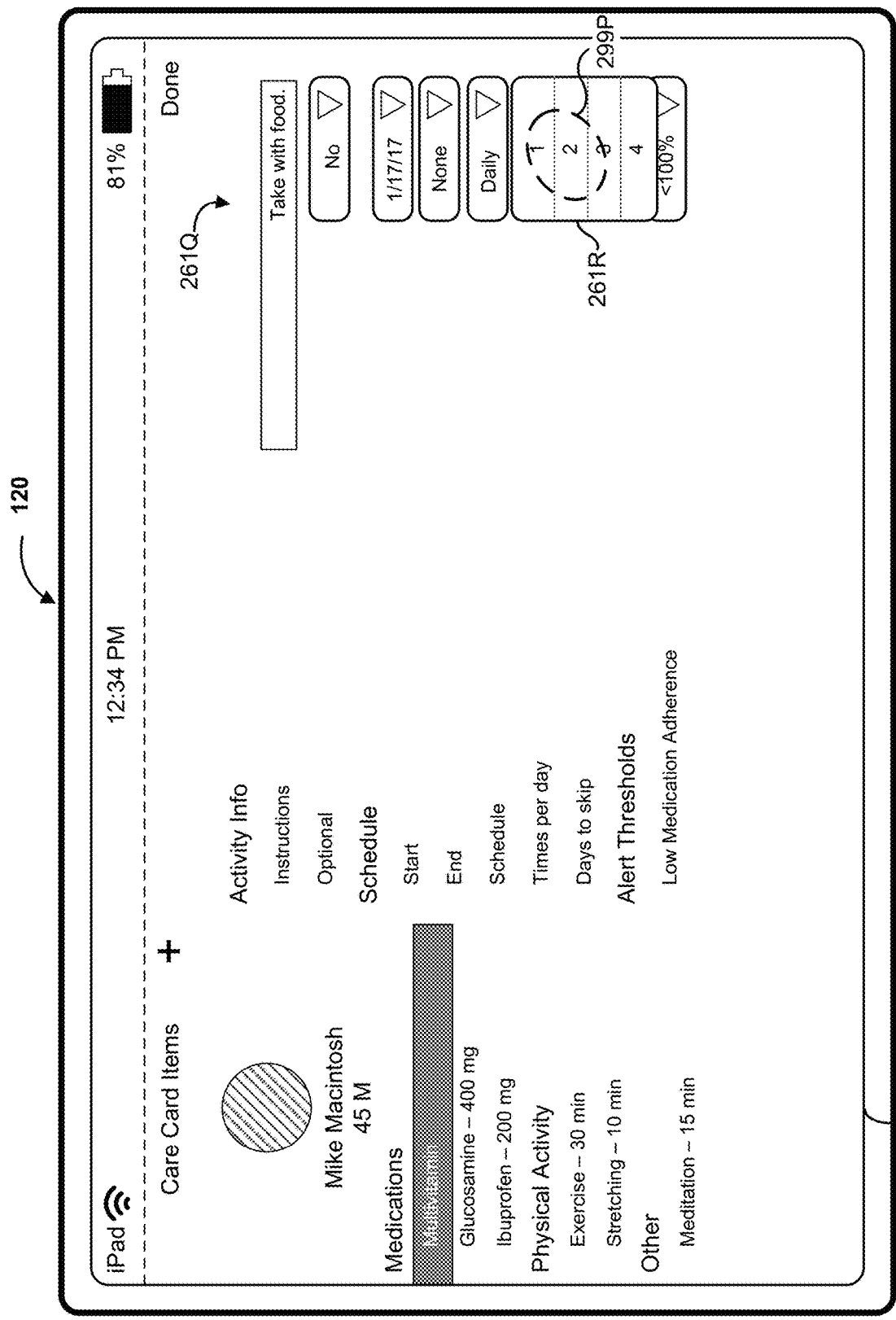

FIG. 2R illustrates the health manager user interface 200 of FIG. 2Q in response to detecting the contact 299O at the location of the option for changing the number of times a day an activity is expected to be completed. In FIG. 2R, the option for changing the number of times a day an activity is expected to be completed is expanded into a dropdown menu 261R listing a variety of numbers that can be selected as the number of times a day. FIG. 2Q illustrates a contact 299P at the location of an option to change the number of times a day to two.

Figure 2S:
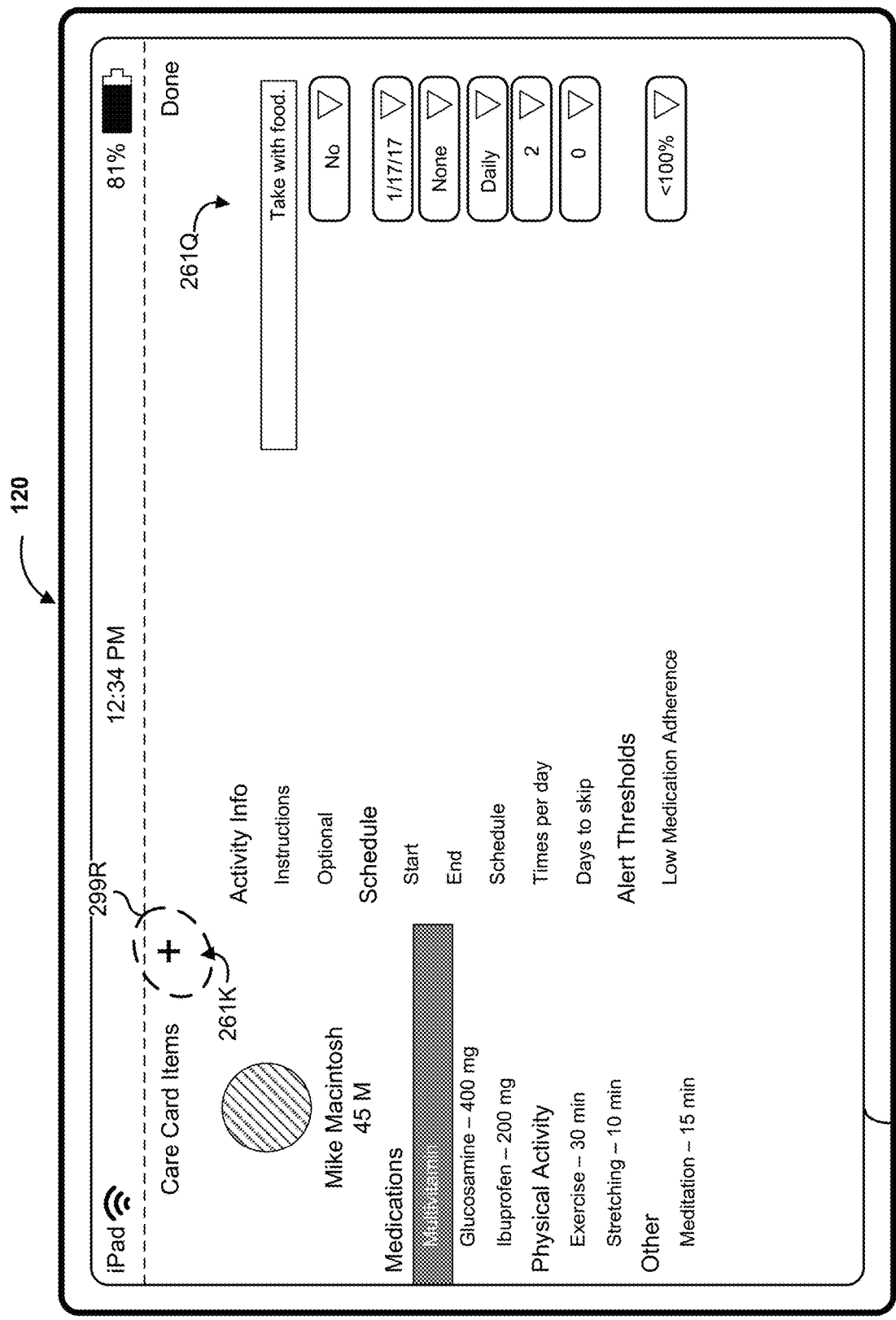

FIG. 2S illustrates the health manager user interface 200 of FIG. 2R in response to detecting the contact 299P at the location of the option to change the number of times a day to two. In FIG. 2S, the option for changing the number of times a day an activity is expected to be completed indicates that the number has been changed to 2. FIG. 2S illustrates a contact 299R at a location of the add item affordance 261K.

Figure 2T:
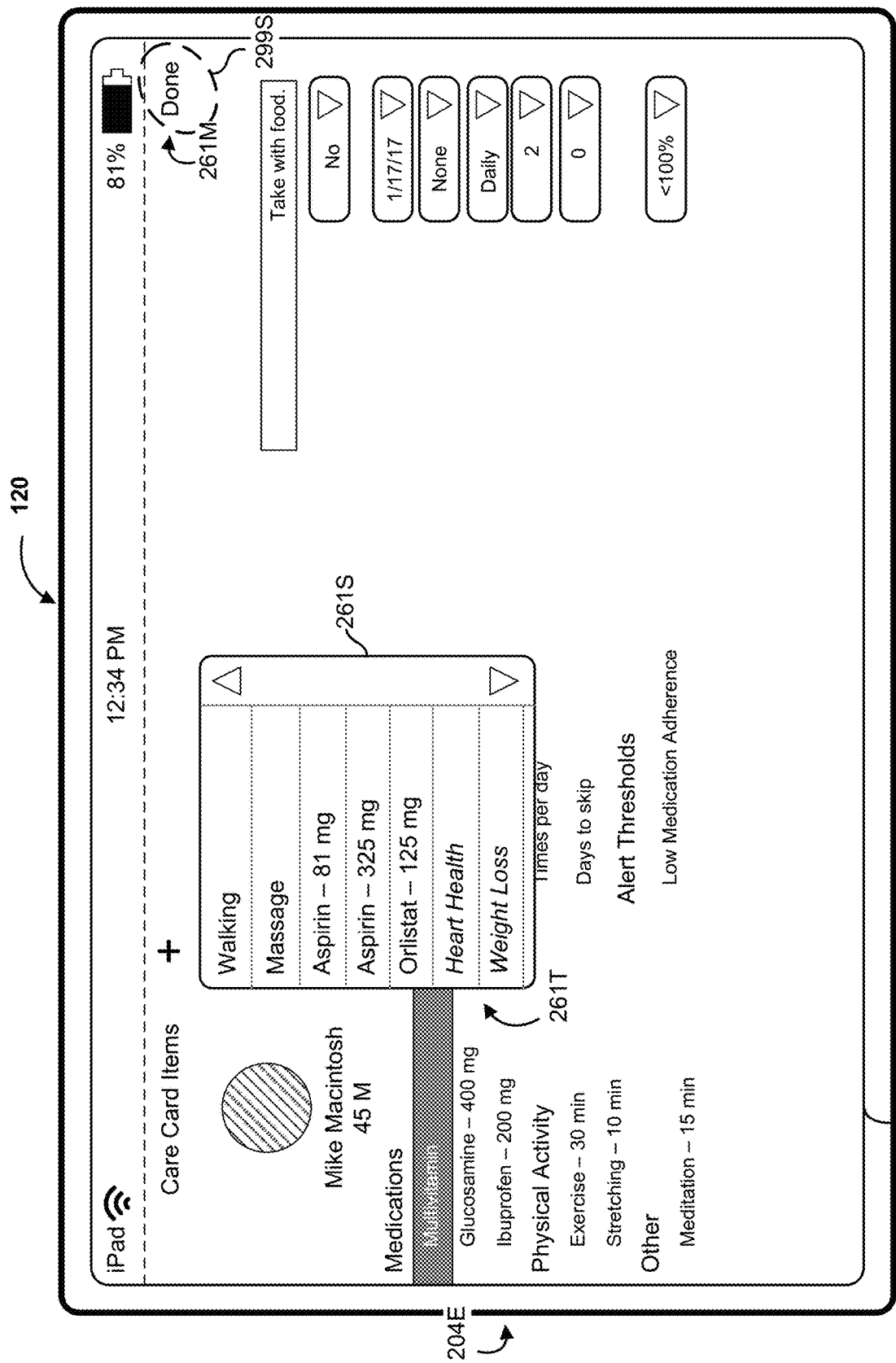

FIG. 2T illustrates the health manager user interface 200 of FIG. 2S in response to detecting the contact 299R at the location of the add item affordance 261K. In FIG. 2T, an item menu 261S is displayed with options to add various activities to the activity listing. Further, the item menu 261S includes options 261T to add item templates to the activity listing. Upon selection of an item template, two or more activities are added to the activity listing. For example, selecting an item template for heart health can include adding a walking activity and an 81 mg aspirin activity. As another example, selecting an item template for insomnia can include adding a meditation activity and a melatonin activity. FIG. 2T illustrates a contact 299S at a location of the return affordance 261M.

Figure 2U:
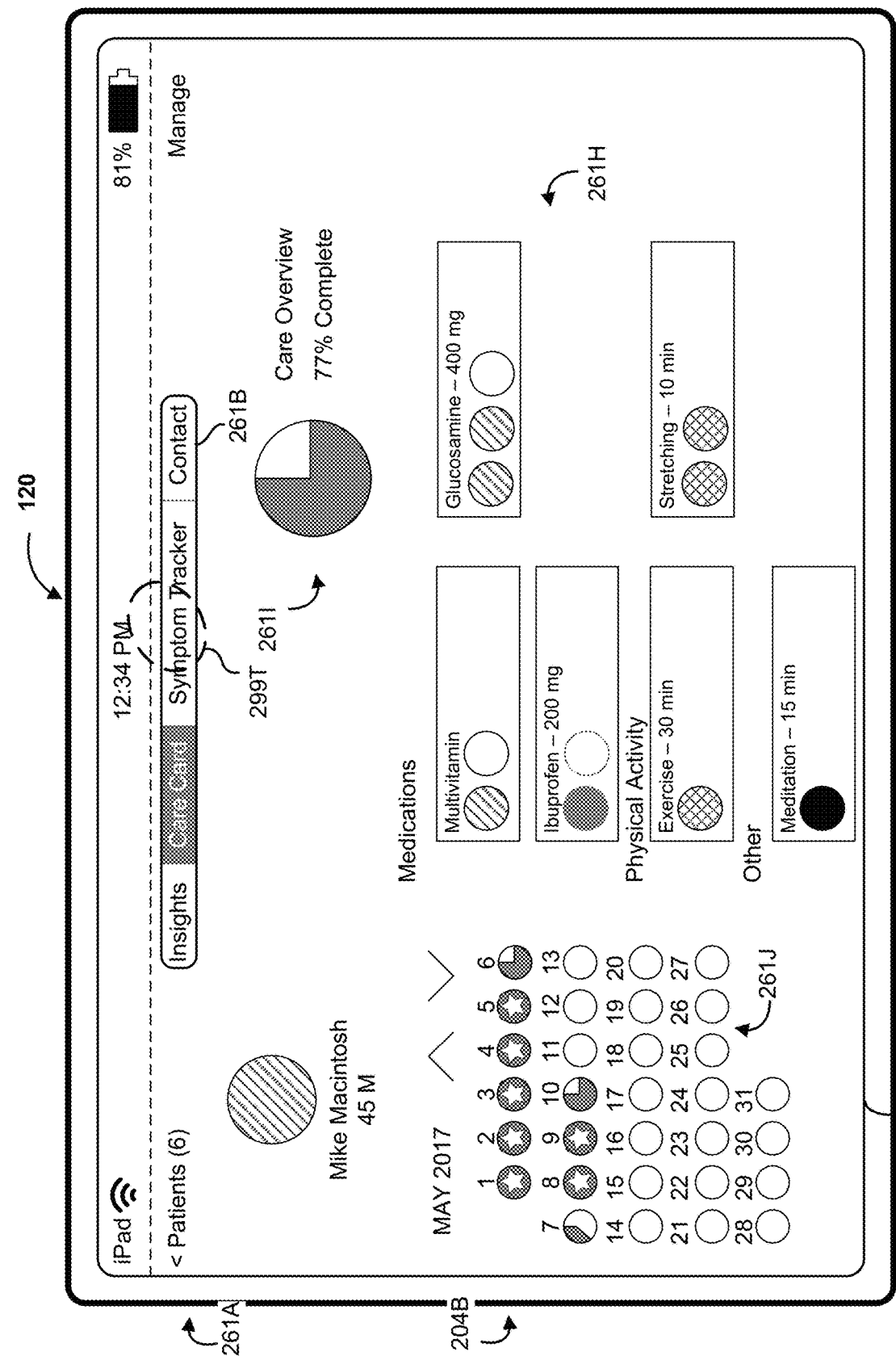

FIG. 2U illustrates the health manager user interface 200 of FIG. 2T in response to detecting the contact 299S at the location of the return affordance 261M. FIG. 2U illustrates the care card user interface 504B. In response to editing the activity details, the activity indicia 261H associated with taking a multivitamin includes two activity indicia (one completed and one uncompleted). Further, the daily percentage indicator 261I has decreased (as also reflected on the same date in the activity adherence calendar 261J) due to the new uncompleted activity. FIG. 2U illustrates a contact 299T detected at a location of the user interface switch affordance 261B to switch to the symptom tracker user interface 204C.

Figure 2V:
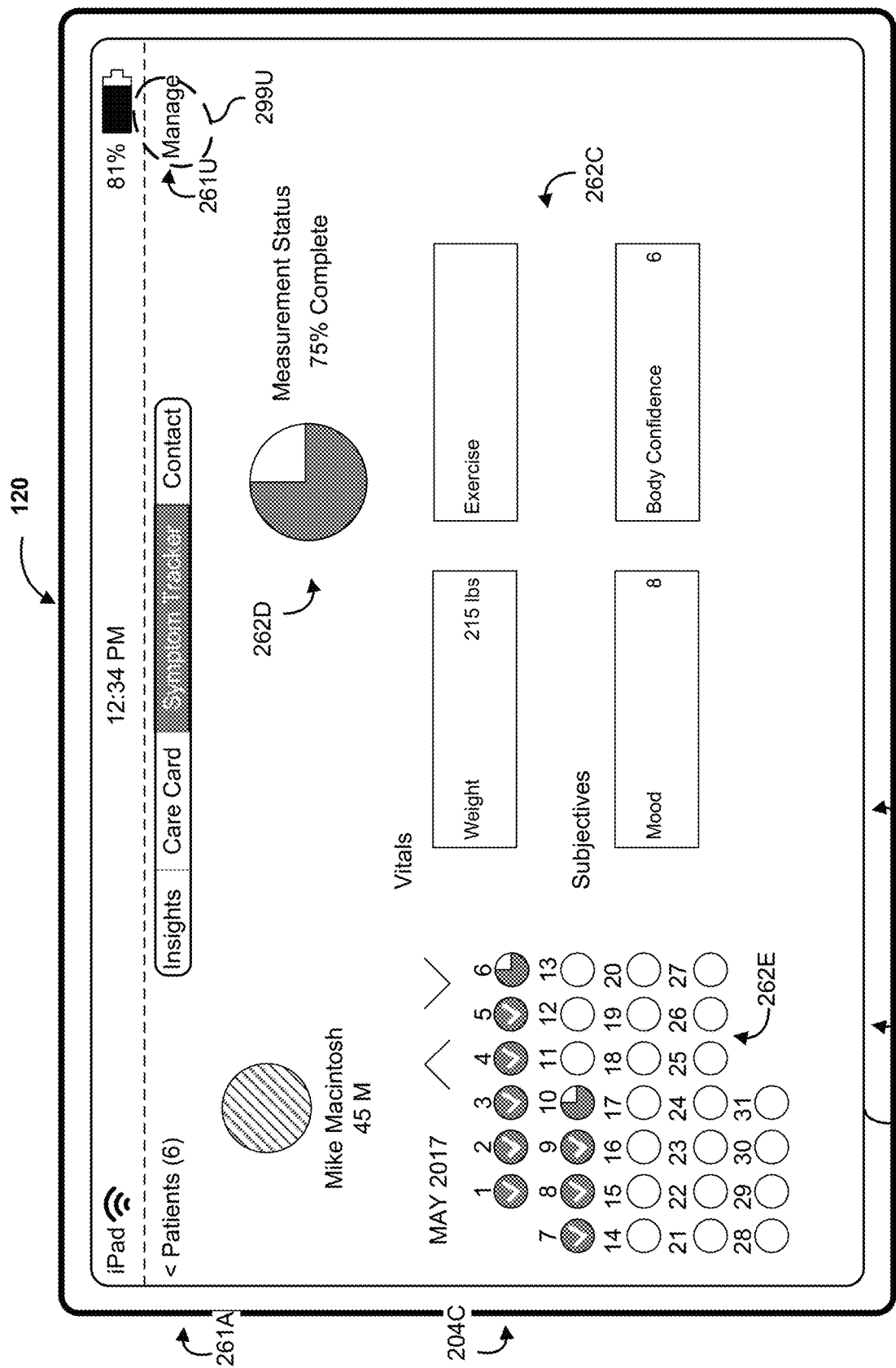

FIG. 2V illustrates the health manager user interface 200 of FIG. 2U in response to detecting the contact 299T at the location of the user interface switch affordance 261B to switch to the symptom tracker user interface 204B. In FIG. 2V, the care card user interface 204B is replaced with the symptom tracker user interface 204C. The symptom tracker user interface 204C includes the user interface switch bar 261A. In the symptom tracker user interface 204C, the user interface switch bar 261A includes a manage affordance 261U for switching to a symptom tracker management user interface 204F, described further below.

The symptom tracker user interface 204C includes a historical measurement adherence region 262A and a daily measurement adherence region 262B. The daily measurement adherence region 262B includes a plurality of measurement indicia 262C corresponding to measurements the patient is expected to take on a particular date. In various implementations, the measurement indicia 262C further include optional measurement indicia corresponding to optional measurements the patient may take, but are not expected to take.

In various implementations, the measurement indicia 262C are organized into sets (e.g., by measurement type (e.g., vitals and subjectives)). In various implementations, different sets of measurement indicia 262C are displayed in a different color, size, shape, or font. In various implementations, measurement indicia 262C associated with measurements that the patient has taken are displayed in a different manner than measurement indicia 262C associated with measurements that the patient has yet to take. For example, the measurement indicia 262C associated with weight is displayed with a value (e.g., 215 lbs) and the measurement indicia 262C associated with exercise is displayed without a value. In various implementations, measurement indicia 262C associated with taken measurements are displayed in a different color, size, shape or font than measurement indicia 262C associated with untaken measurements.

In various implementations, the measurement can take the form of a numerical value (e.g., a heart rate measurement). In various implementations, the measurement can take the form of multiple numerical values (e.g., a blood pressure measurement including a systolic value and a diastolic value). In various implementations, the measurement can take the form of an audio recording (e.g., the sound of a breathing irregularity). In various implementations, the measurement can take the form of a photograph or a video (e.g., a photograph of a healing wound).

The daily measurement adherence region 262B includes a daily percentage indicator 262D that indicates the percentage of taken measurements of the measurements the patient is expected to take on a particular date. In various implementations, the daily percentage indicator 262D includes a textual and/or a graphical indicator.

The historical measurement adherence region 262A includes patient identifying information (such as a profile picture, a name, age, and gender). The historical measurement adherence region 262A includes a measurement adherence calendar 262E including daily percentage indicators for a variety of dates (e.g., for each date in a particular month). In various implementations, daily percentage indicators of the calendar (and, optionally, the daily percentage indicator 262D in the daily measurement adherence region 262B) that are 100% complete (or at least greater than a predefined threshold) are displayed with a completion indicator, such as a star or a checkmark.

FIG. 2V illustrates a contact 299U detected at a location of the manager affordance 261U.

Figure 2W:
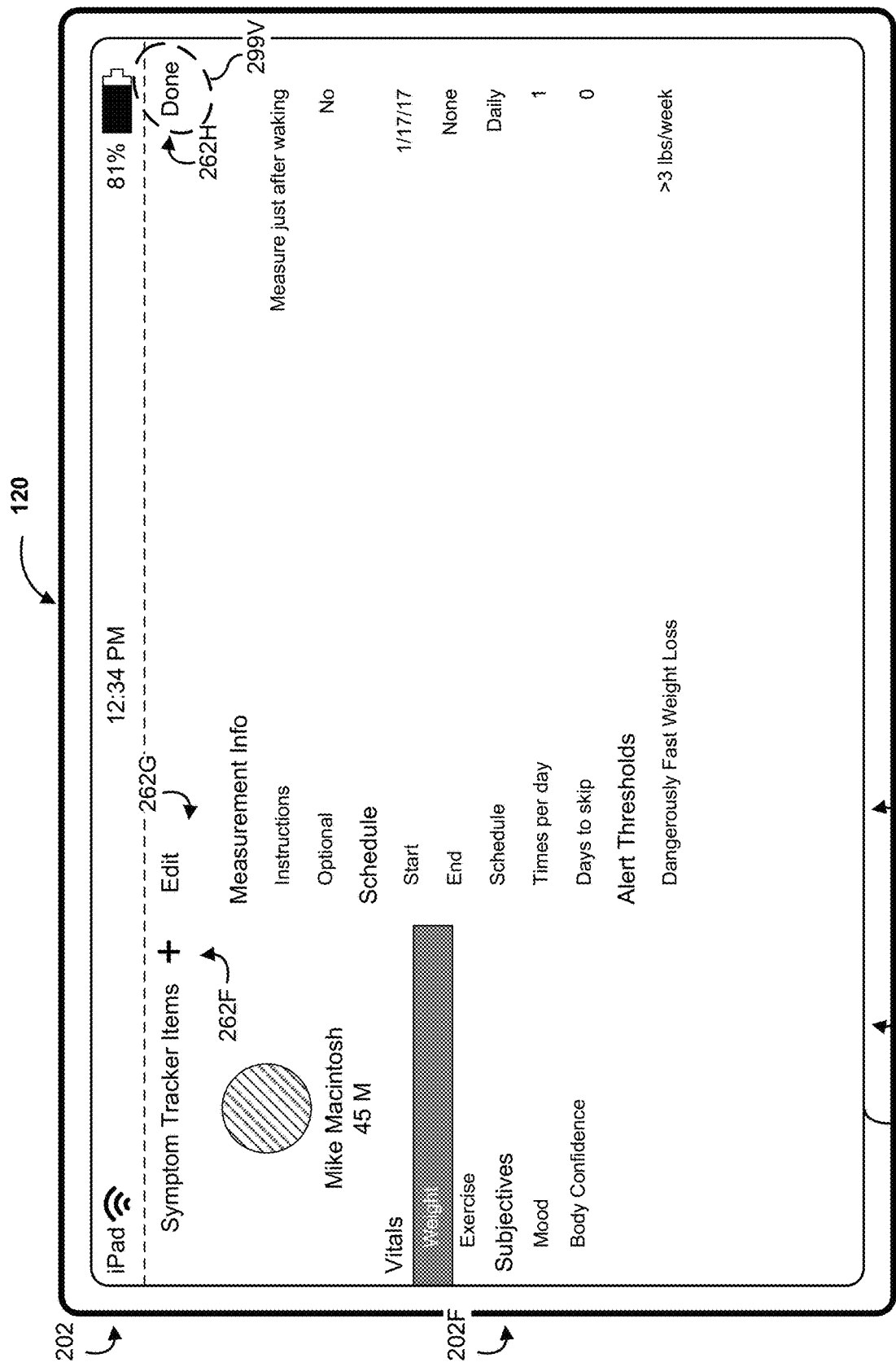

FIG. 2W illustrates the health manager user interface 200 in response to detecting the contact 299U at the location of the manager affordance 261U. In FIG. 2W, the health manager user interface 200 includes, beneath the device bar 202, the symptom tracker management user interface 204F. The symptom tracker management user interface 204F includes a measurement listing region 262I that includes patient identifying information and a measurement listing. The measurement listing includes an entry for each measurement the patient is expected to take, regardless of date. The symptom tracker management user interface 204F includes a measurement details region 262J that includes details regarding a measurement selected from the measurement listing. In various implementations, the measurement details indicate whether the measurement is optional or not. In various implementations, the measurement details include a schedule at which the measurement is expected to be taken. In various implementations, the measurement details include a threshold at which an alert is generated for the measurement.

The symptom tracker management user interface 204F includes an add item affordance 262F for adding one or more measurements to the measurement listing, an edit item affordance 262G for editing the details of the measurement selected from the activity listing, and a return affordance 262H for returning to the symptom tracker user interface 204C. FIG. 2W illustrates a contact 299V detected at a location of the return affordance 262H.

Figure 2X:
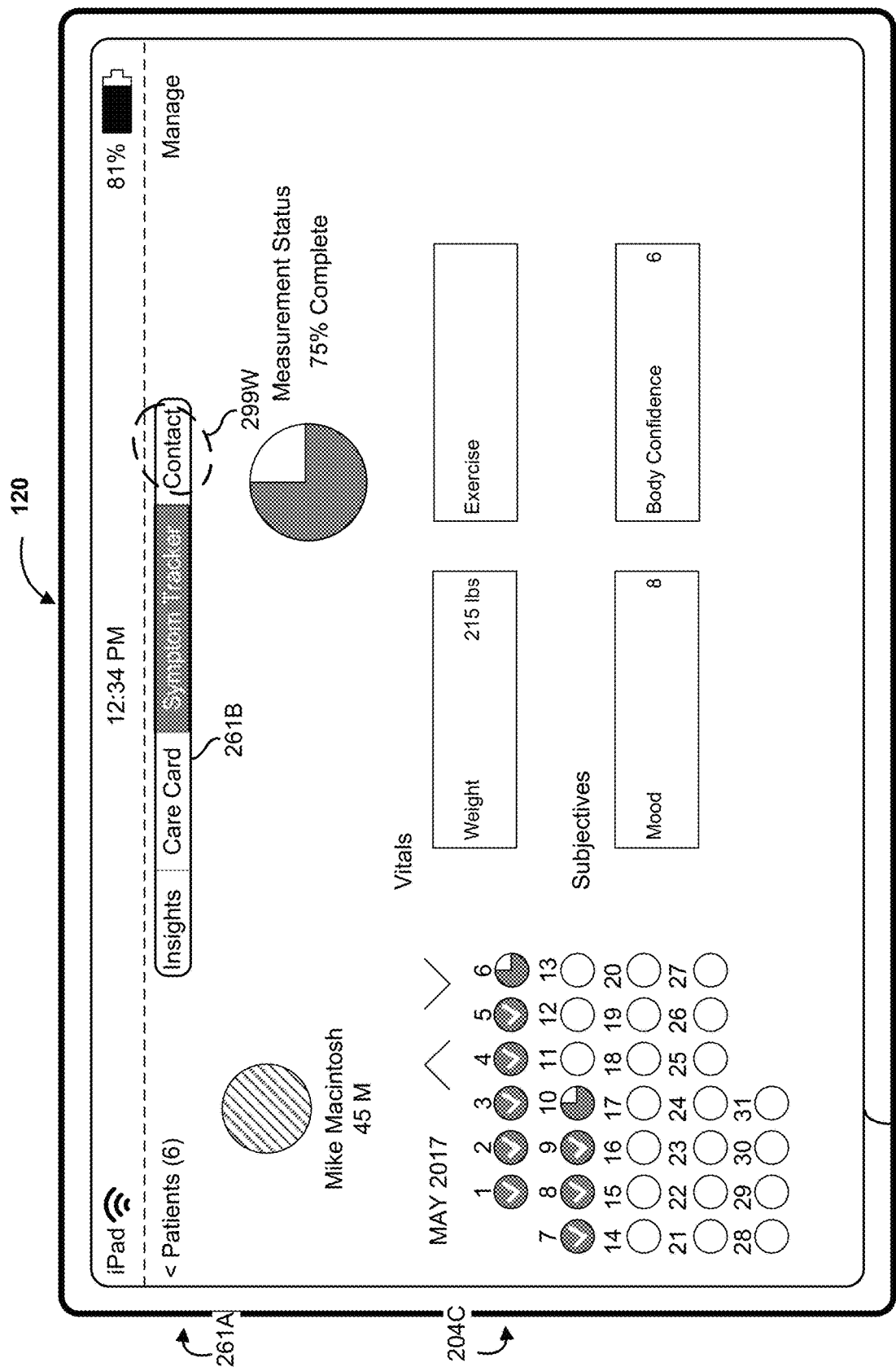

FIG. 2X illustrates the health manager user interface 200 in response to detecting the contact 299V at the location of the return affordance 262H. FIG. 2X illustrates the symptom tracker user interface 204C (identical to the symptom tracker user interface 204C in FIG. 2V). FIG. 2X illustrates a contact 299W detected at a location of the user interface switch affordance 261B to switch to the contact user interface 204D.

Figure 2Y:
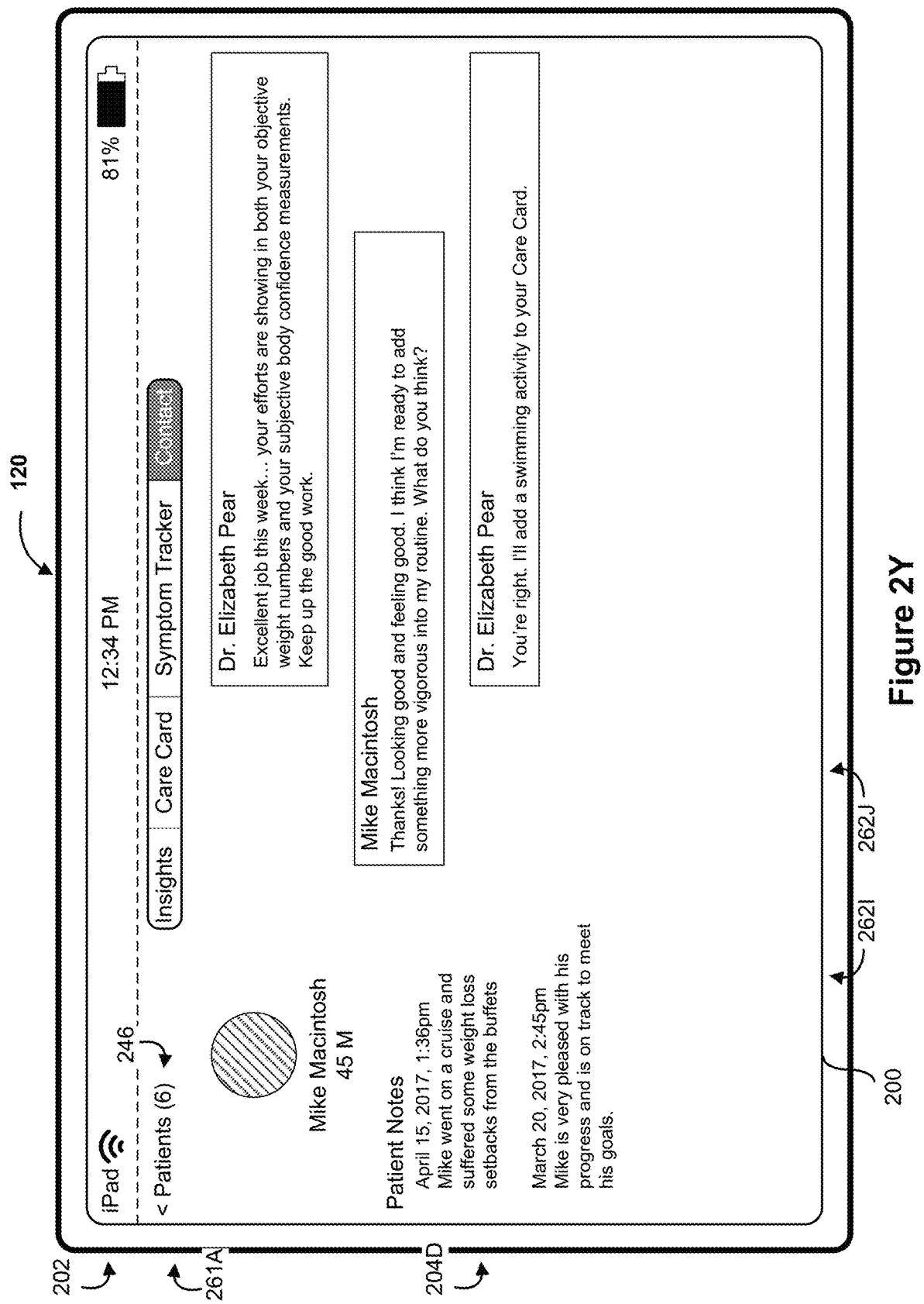

FIG. 2Y illustrates the health manager user interface 200 in response to detecting the contact 299W at the location of the user interface switch affordance 261B to switch to the contact user interface 204D. In FIG. 2Y, the symptom tracker user interface 204C is replaced with the contact user interface 204D. The contact user interface 204D includes the user interface switch bar 261A, including the return affordance 246.

The contact user interface 204D includes a patient history region 262I and a messaging region 262J. The patient history region 262I includes patient identifying information (such as a profile picture, a name, age, and gender). In various implementations, which patient identifying information is displayed in the patient history region 261I is customizable. In various implementations, the patient history region 262I includes timestamped patient notes. The messaging region 262J includes messages exchanged between the patient and the health manager.

Figure 2Z:
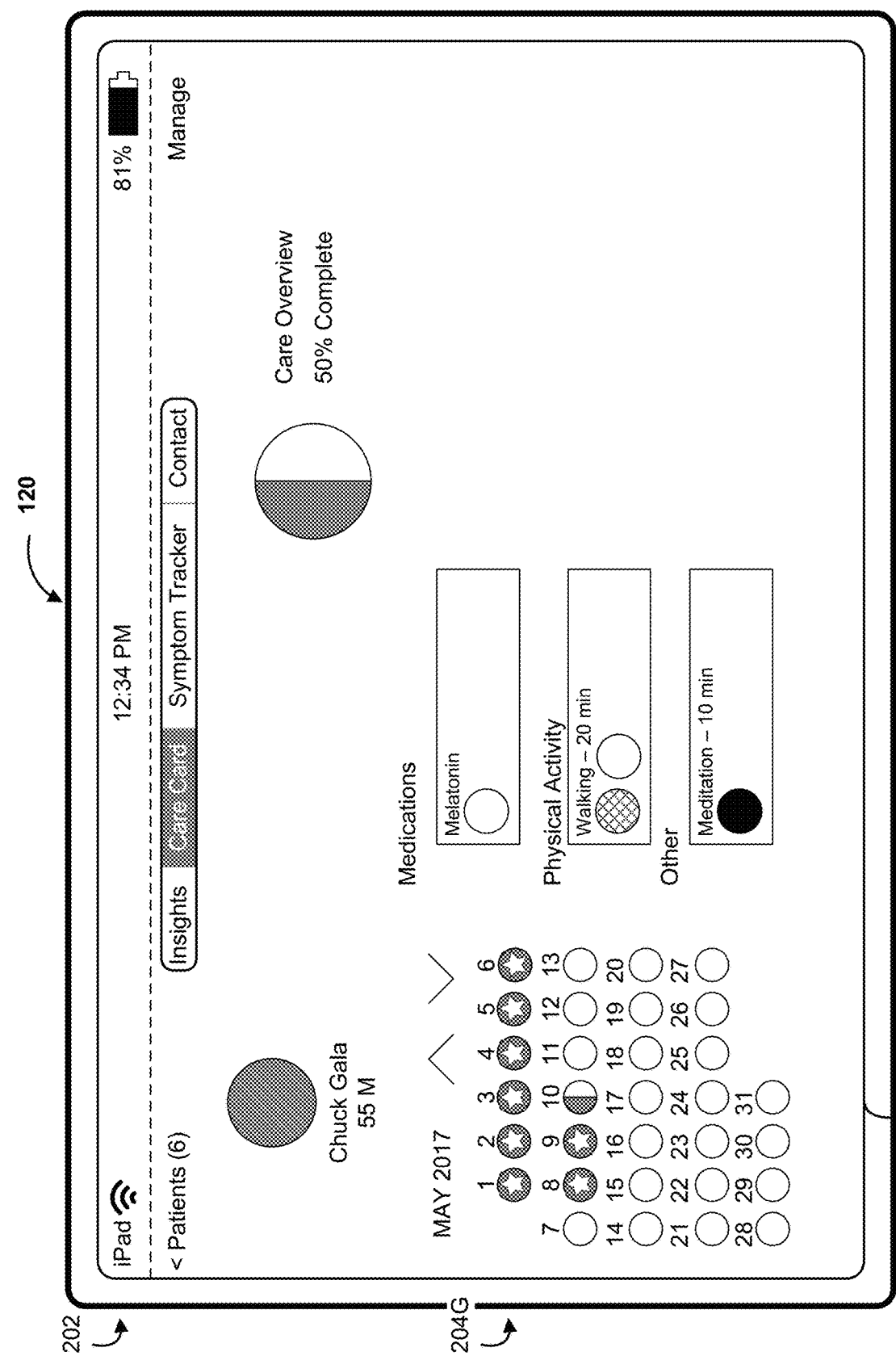

FIG. 2Z illustrates the health manager user interface 200 including a care card user interface 204G for another patient. The care card user interface 204G is substantially similar to the care card user interface 204B, but illustrates activities for a different patient.

Figure 3A:
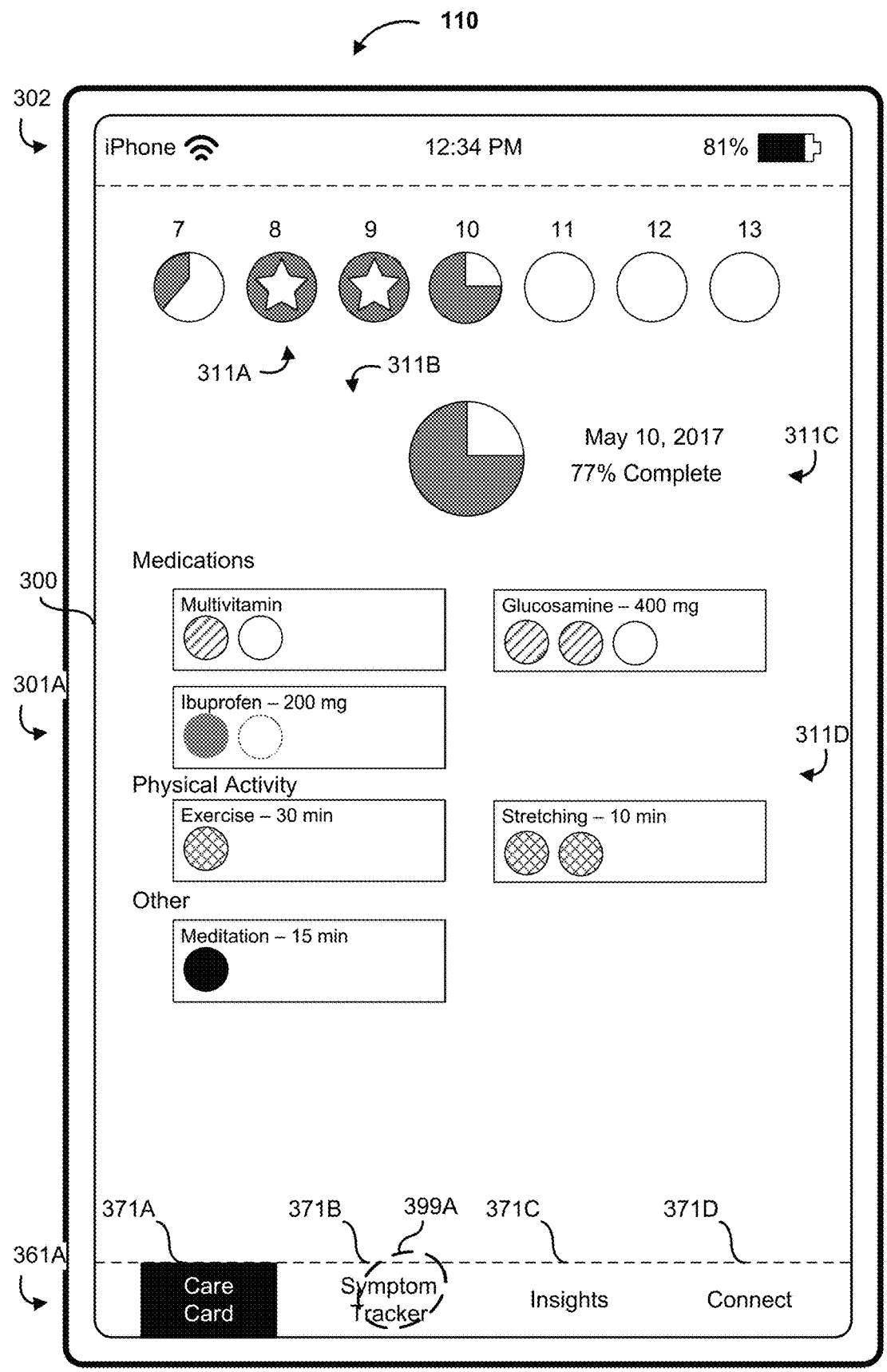
FIGS. 3A-3D illustrate a patient user interface in accordance with some implementations.

FIG. 3A illustrates a patient user interface 300 in accordance with some implementations. FIG. 3A illustrates the health manager user interface 300 including a care card user interface 201A below a device bar 202. The device bar 302 at the top of the display includes an identifier of the first patient device 110 (e.g., "iPhone"), a wireless connection indicator, a current time, and a battery indicator indicating a charge level of the first patient device 110. The patient user interface 300 includes, below the device bar 302, and spanning the rest of the display, a care card user interface 301A.

The care card user interface 301A includes a historical activity adherence region 311A and a daily activity adherence region 311C. The daily activity adherence region 311C includes a plurality of activity indicia 311D corresponding to activities the patient is expected to complete on a particular date. The daily activity adherence region 311B includes a daily percentage indicator 311C that indicates the percentage of completed activities of the activities the patient is expected to complete on a particular date. In various implementations, the daily percentage indicator 311C includes a textual and/or a graphical indicator. As shown in FIG. 3A, the activity indicia 311D correspond to the activity indicia 261H of the health manager user interface 200 of FIG. 2U including indication of a completion of the second stretching activity (changed in response to contact 299L in FIG. 2N) and the addition of the second multivitamin activity (added in response to the contact 299P of FIG. 2R). Accordingly, when a health manager makes changes to the activities of a treatment plan, the changes are reflected in near real-time on the patient device 110. Similarly, when the patient indicates that an activity is complete (e.g., by touching the activity indicia 311D), the activity indicia 261H of the health manager user interface 200 of FIG. 2U are updated in near real-time on the health manager device 120.

The historical activity adherence region 311A includes an activity adherence calendar including daily percentage indicators for a variety of dates (e.g., for each date in a particular week). In various implementations, daily percentage indicators of the calendar (and, optionally, the daily percentage indicator 311C in the daily activity adherence region 311B) that are 100% complete (or at least greater than a predefined threshold) are displayed with a completion indicator, such as a star or a checkmark.

The care card user interface 301A includes a user interface switch bar 361A for switching between various user interfaces. The user interface switch bar 361A includes a care card user interface affordance 371A for switching to the care card user interface 301A, a symptom tracker user interface affordance 371B for switching to a symptom tracker user interface 301B, an insights user interface affordance 371C for switching to an insights user interface 301C, and a connect user interface affordance 371D for switching to a connect user interface 301D. FIG. 3A illustrates a contact 399A detected at the location of the symptom tracker user interface affordance 371B.

Figure 3B:
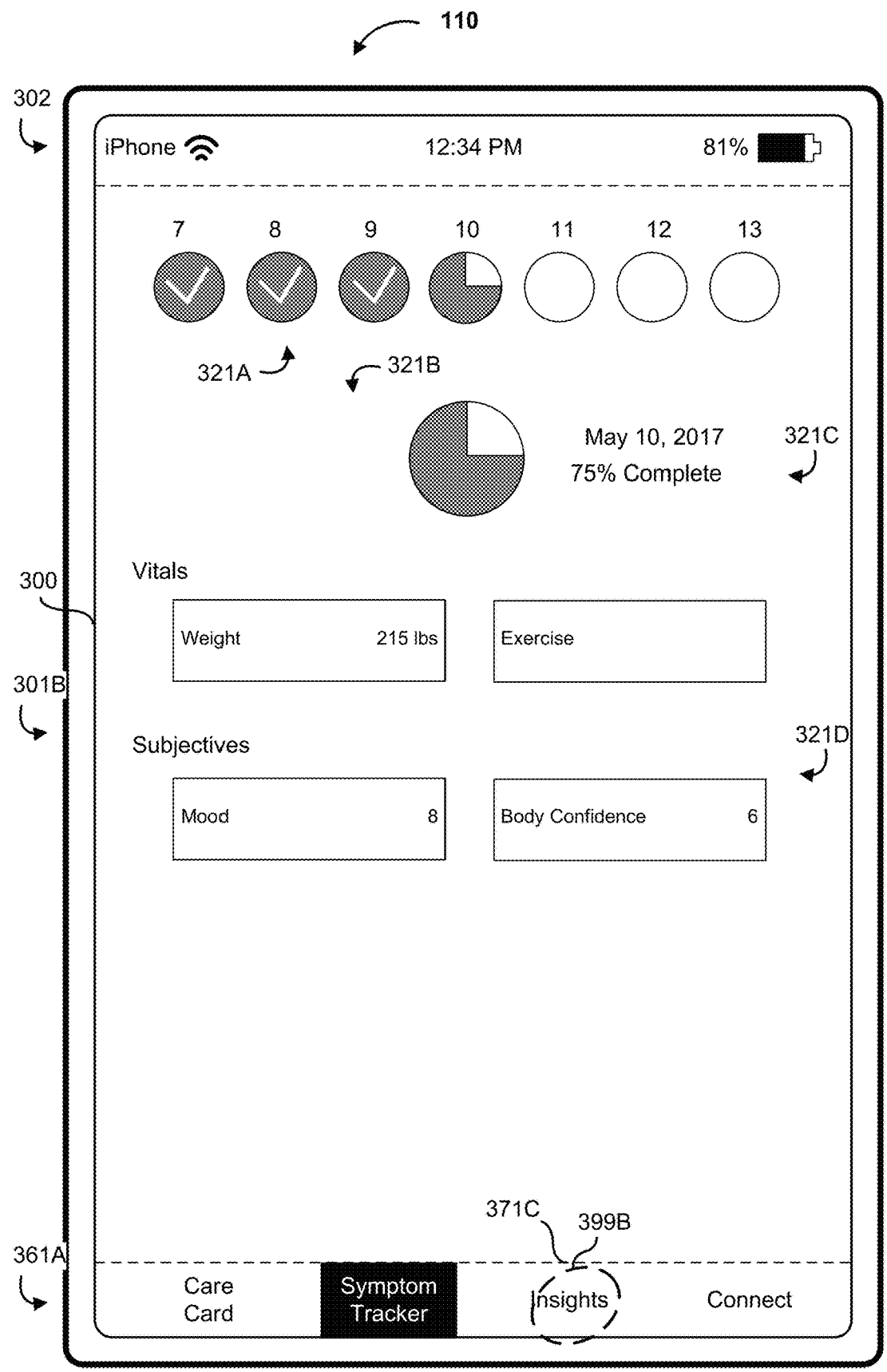

FIG. 3B illustrates the patient user interface 300 in response to detecting the contact 399A at the location of the symptom tracker user interface affordance 371B. In FIG. 3B, the care card user interface 301A is replaced with a symptom tracker user interface 301B. The symptom tracker user interface 301B includes a historical measurement adherence region 321A and a daily measurement adherence region 321B. The daily measurement adherence region 321B includes a plurality of measurement indicia 321D corresponding to measurements the patient is expected to take on a particular date. The daily measurement adherence region 321B includes a daily percentage indicator 321C that indicates the percentage of taken measurements of the measurements the patient is expected to complete on a particular date. In various implementations, the daily percentage indicator 321C includes a textual and/or a graphical indicator. In various implementations, measurements are taken automatically by an external device coupled to the patient device 110, such as a wearable health tracker. In various implementations, measurements are taken by a patient and input via the symptom tracker user interface (e.g., by touching the measurement indicia 321D and inputting a corresponding value). In various implementations, when a measurement is input on the patient device 110, the measurement indicia 262C of the health manager user interface 200 of FIG. 2V are updated in near real-time on the health manager device 120.

The historical measurement adherence region 321A includes a measurement adherence calendar including daily percentage indicators for a variety of dates (e.g., for each date in a particular week). In various implementations, daily percentage indicators of the calendar (and, optionally, the daily percentage indicator 321C in the daily activity adherence region 311B) that are 100% complete (or at least greater than a predefined threshold) are displayed with a completion indicator, such as a star or a checkmark.

The symptom tracker user interface 301B includes the user interface switch bar 361A for switching between various user interfaces. FIG. 3B illustrates a contact 399B detected at a location of the insights user interface affordance 371C.

Figure 3C:
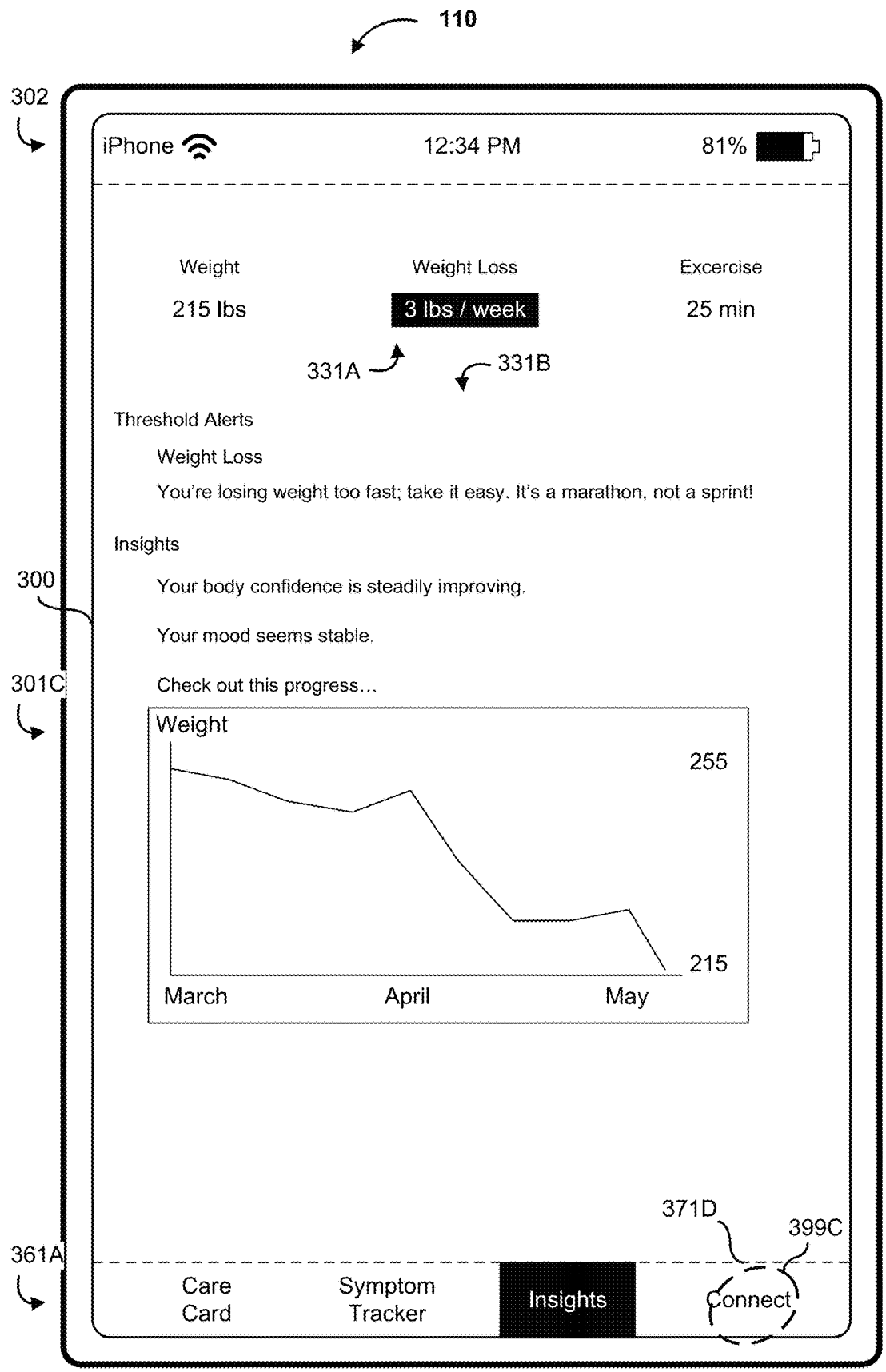

FIG. 3C illustrates the patient user interface 300 in response to detecting the contact 399B at the location of the insights user interface affordance 371C. In FIG. 3C, the symptom tracker user interface 301B is replaced with an insights user interface 301C. The insights user interface 301C includes a patient health metric region 331A and an insights region 331A. The patient health metric region 331A includes representations of values of various health metric types of the patient (referred to herein as "health widgets"). In various circumstances, the value for a health metric type exceeds an alert threshold. For example, the weight loss health metric exceeds a threshold and the corresponding health widget is displayed in a different manner than other representations. For example, in various implementations, the health widget is displayed in a different color, a different font, a different size, a different background color (highlighting), or with any other visual alert indication. The insights region 331B includes both textual information and graphical information regarding the health of the patient.

The insights user interface 301C includes the user interface switch bar 361A for switching between various user interfaces. FIG. 3C illustrates a contact 399C detected at a location of the connect user interface affordance 371D.

Figure 3D:
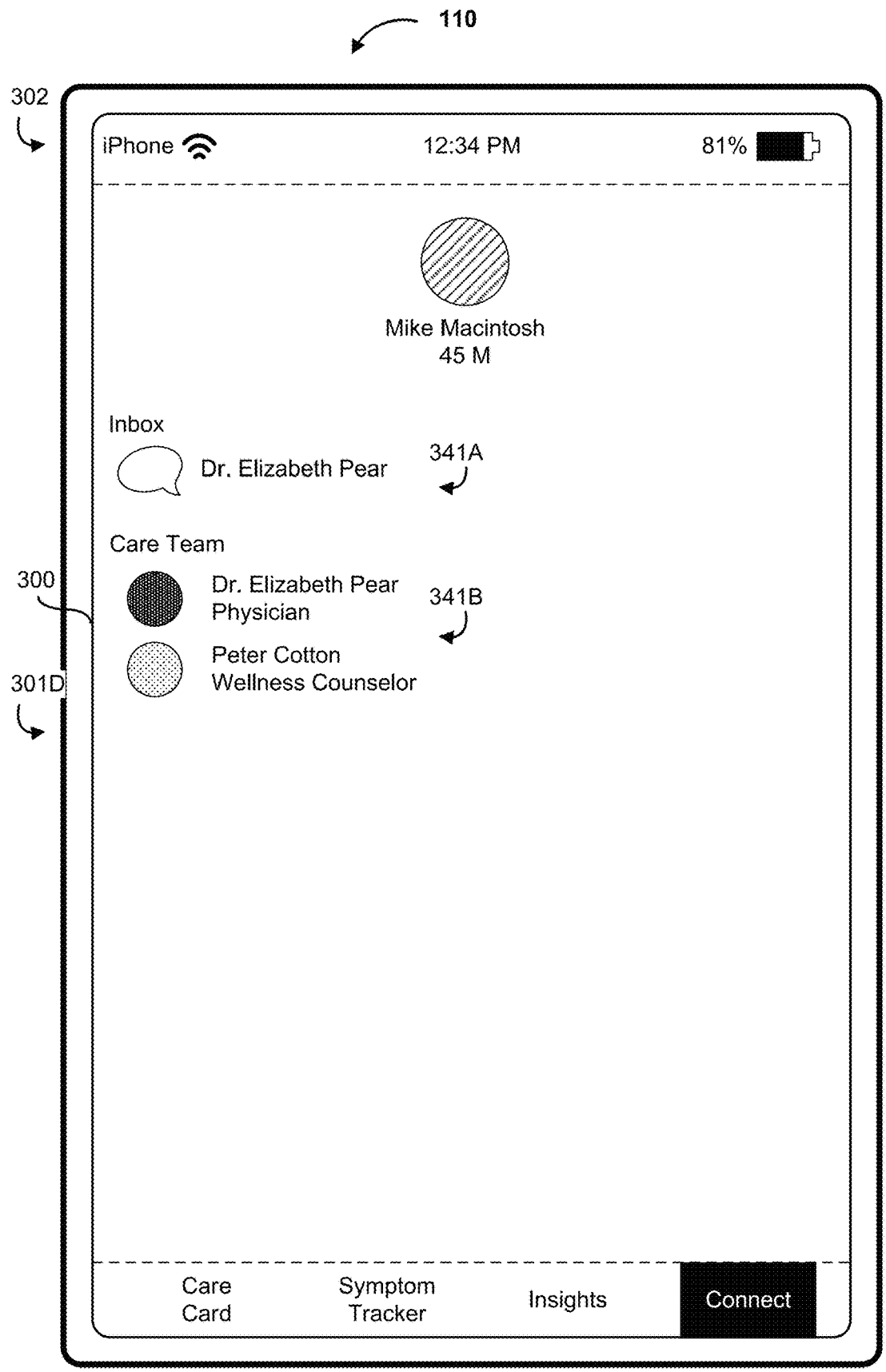

FIG. 3D illustrates the patient user interface 300 in response to detecting the contact 399C at the location of the connect user interface affordance 371D. In FIG. 3D, the insights user interface 301C is replaced with a connect user interface 301D. The connect user interface includes one or more inbox affordances 341A and one or more contact card affordances 341B. In response to detecting selection of one of the contact card affordances 341B, the first patient device 110 displays a contact card user interface including contact information of a treating health manager. In response to detecting selection of one of the inbox affordances 341A, the first patient device 110 displays a messaging user interface allowing secure communication with the selected health manager.

Figure 4:
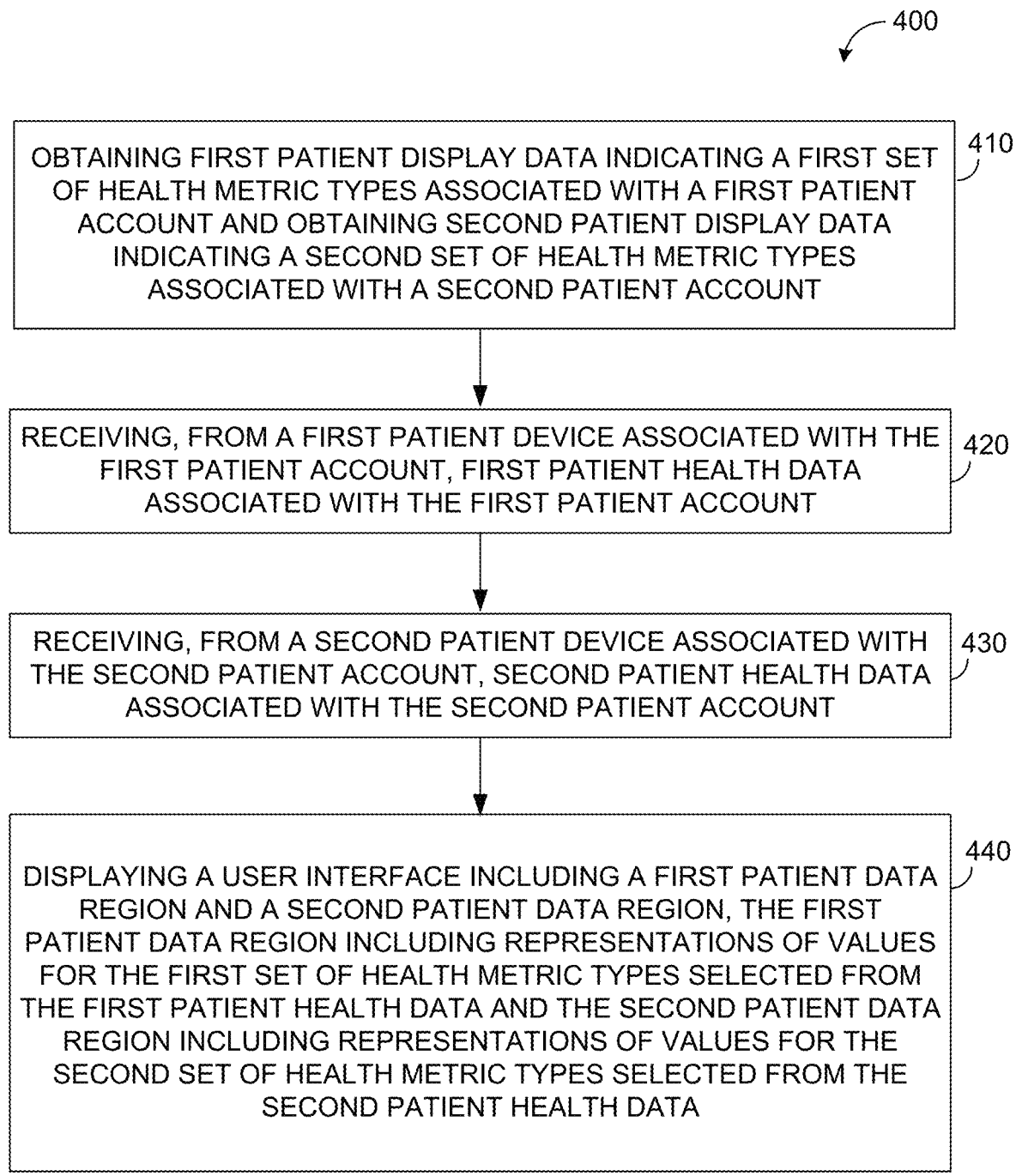
FIG. 4 is a flowchart representation of a method of displaying patient health information in accordance with some implementations.

FIG. 4 is a flowchart representation of a method 400 of displaying patient health information in accordance with some implementations. In some implementations (and as detailed below as an example), the method 400 is performed by an electronic device (or a portion thereof), such as the health manager device 120 of FIG. 1. In some implementations, the method 400 is performed at a health manager device, associated with a health manager account, with one or more processors, non-transitory memory, a network interface, a display, and one or more input devices. In various implementations, the display is integrated with one of the input devices as a touch-sensitive display. In some implementations, the method 400 is performed by processing logic, including hardware, firmware, software, or a combination thereof. In some implementations, the method 400 is performed by a processor executing code stored in a non-transitory computer-readable medium (e.g., a memory). Briefly, the method 400 includes obtaining first and second patient display data, receiving first and second patient health data, and displaying first and second patient data regions including representations of patient health data selected based on the patient display data.

The method 400 begins, at block 410, with the electronic device obtaining first patient display data indicating a first set of health metric types associated with a first patient account and second patient display data indicating a second set of health metric types associated with a second patient account. In various implementations, the first patient display data and the second patient display data are received via a network interface, e.g., from a secure cloud storage system. In various implementations, the first patient display data and the second patient display data are stored locally in non-transitory memory of the electronic device.

In various implementations, the first patient display data indicates which health widgets are to be displayed in a patient management user interface, such as the patient management user interface 201 of FIG. 2A. As noted above, in various implementations, different health widgets are displayed for different patients. For example, in FIG. 2A, a first patient health metric region 212A includes a glucose health widget and a heart rate health widget whereas a second patient health metric region 212B includes an exercise health widget and a weight health widget. Accordingly, in various implementations, the first set of health metric types (indicated by the first patient health data) is different from the second set of health metric types (indicated by the second patient health data).

In various implementations, the first patient display data (and, in a similar manner, the second patient display data) can be changed by a health manager interacting with the electronic device. In one embodiment, the electronic device detects, via one or more input devices, a request to edit the first patient display data. For example, in FIG. 2H, the device detects a contact 299F at a location of the health widget edit affordance 245. In response to detecting the request to edit the first patient display data, the device displays a widget edit user interface including options to edit the first patient display data. For example, in FIG. 2I, the device displays a widget edit user interface 203 including a widget data edit region 251A. In various implementations, the options to edit the first patient display data include an option to display a list of selectable health metric types. In various implementations, the options to edit the first patient display data include an option to set an alert threshold associated with one of the first set of health metric types.

The method 400 continues, at block 420, with the electronic device receiving, from a first patient device associated with the first patient account, first patient health data associated with the first patient account. In various implementations, the first patient health data is received via a network interface. The first patient health data can be received directly from the first patient device (over a network) or retrieved from a secure cloud storage system after being stored there by the first patient device. In various implementations, the first patient health data includes values of various biometric measurements, such as heart rate, respiratory rate, hours of sleep, minutes of exercise, weight, blood sugar level, etc. In some embodiments, the biometric measurements are input by a user into the first patient device. In some embodiments, the biometric measurements are provided automatically to the first patient device by an external device, such as heart rate monitor or fitness watch.

The method 400 continues, at block 430, with the electronic device receiving, from a second patient device associated with the second patient account, second patient health data associated with the second patient account. The second patient health data can be received directly from the second patient device (over a network) or retrieved from a secure cloud storage system after being stored there by the second patient device. In various implementations, the second patient health data includes values of various biometric measurements, such as heart rate, respiratory rate, hours of sleep, minutes of exercise, weight, blood sugar level, etc. In some embodiments, the biometric measurements are input by a user into the second patient device. In some embodiments, the biometric measurements are provided automatically to the second patient device by an external device, such as heart rate monitor or fitness watch.

The method 400 continues, at block 440, with the electronic device displaying a user interface including a first patient data region and a second patient data region, the first patient data region including representations of values for the first set of health metric types selected from the first patient health data and the second patient data region including representations of values for the second set of health metric types selected from the second patient health data. For example, in FIG. 2A, the health manager device 120 displays a patient management user interface 201 that includes a first patient data region 212A and a second patient data region 212B.

The first patient data region include representations of values for a set of first health metric types selected from the first patient health data. Accordingly, in various implementations, the electronic device receives many biometric measurements from the first patient device in the first patient health data and displays only a subset of the biometric measurements in the user interface, those dictated by the first patient display data. As the first patient display data and second patient display data can be edited, a user can customize which biometric measurements are displayed for each patient.

In various implementations, the first patient data region includes more than the representations of values for the set of first health metric types. For example, in various implementations, the first patient data region includes patient identifying information, such as a profile picture or other visual identifier of the patient, a name of the patient or other textual identifier of the patient (including, for example, an age and/or gender of the patient), and treating health managers of the patient. In various circumstances, first patient data region includes an alert indication that a value of the first patient health data exceeds an alert threshold (e.g., is less than or greater than a prescribed value). In some circumstances, the value of the first patient health data that exceeds the alert threshold is not one of the first set of health metric types. Thus, the alert indication may be only indication on the display of the value of the first patient health data that exceeds the alert threshold. In some circumstances, the value of the first patient health data that exceeds the alert threshold is one of the first set of health metric types. Accordingly, in various implementations, responsive to a respective value for the first set of health metric types exceeding an alert threshold, a respective representation of the value is displayed in a different manner than another representation of a value for the first set of health metric types. For example, in FIG. 2A, the third patient data region 212C includes a sleep widget 231C that is displayed in a different manner than the heart rate widget. In various implementations, displaying in a different manner includes displaying in a different color, a different font, a different size, a different background color (highlighting), or with any other visual alert indication. In various implementations, the alert threshold is different for different patients. For example, the sleep widget 231D of the fourth patient data region 212D is displayed in the same manner as the other widgets. As another example, in FIG. 2B, the sleep widget of the sixth patient data region 210F is displayed in a different manner in response to the value exceeding an alert threshold (e.g., less than 8 hours) that is different than the alert threshold for the first patient data region (e.g., less than 7 hours). Accordingly, in various implementations, responsive to a respective value for the second set of health metric types exceeding a second alert threshold, a respective representation of the value is displayed in a different manner than another representation of a value for the second set of health metric types, wherein the second alert threshold is different than the first alert threshold.

In various implementations, the user interface includes a plurality of patient data regions including the first patient data region and the second patient data region. In various implementations, the plurality of patient data regions includes one or more patient data regions in addition to the first patient data region and the second patient data region. The user interface provides a mechanism to filter the patient data regions displayed in the user interface. In various implementations, the electronic device detects selection of a filter affordance displayed in the user interface. For example, in FIG. 2A, the health manager device 120 detects the contact 299A at a location of the search bar 242A. As another example, in FIG. 2C, the health manager device 120 detects the contact 299B at the location of the filter menu affordance 241. Thus, the filter affordance can be a search bar or a filter menu affordance. In response to detecting selection of the filter affordance, the electronic device displays options to select one or more filter criteria. For example, the electronic device can display a cursor in search bar or display a menu of criteria selection affordances. The electronic device detects selection of one or more filter criteria. In various implementations, the one or more filter criteria includes at least one of a patient categorization criterion, a health manager criterion, an alert-presence criterion, or a search term matching criterion. For example, in FIG. 2B, the health manager device 120 receives a search query 242B. As another example, in FIG. 2E, the health manager device 120 detects a contact 299D detected at a location of the option to filter by gender to display patient data regions associated with male patients. In response to detecting selection of one or more filter criteria, the electronic device ceases to display those of the plurality of patient data regions associated with patient accounts failing to meet the filter criteria. For example, in FIG. 2B, the health manager user interface 201 only includes patient data regions associated with patient accounts matching the search query. As another example, in FIG. 2F, the health manager user interface 201 only includes patient data regions associated with male patients.

Figure 5:
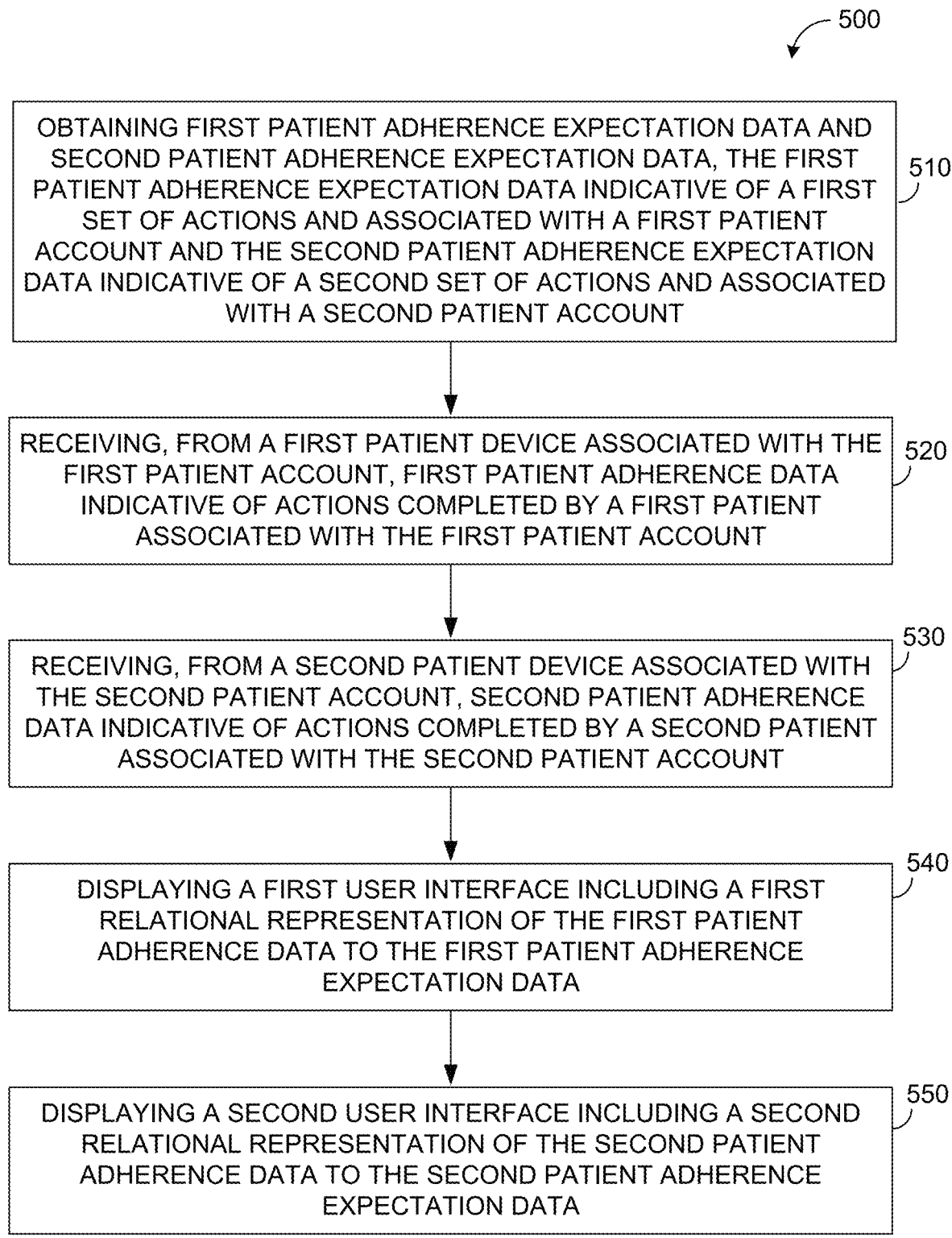
FIG. 5 is a flowchart representation of a method of displaying patient adherence information in accordance with some implementations.

FIG. 5 is a flowchart representation of a method 500 of displaying patient adherence information in accordance with some implementations. In some implementations (and as detailed below as an example), the method 500 is performed by an electronic device (or a portion thereof), such as the health manager device 120 of FIG. 1. In some implementations, the method 500 is performed at a health manager device, associated with a health manager account, with one or more processors, non-transitory memory, a network interface, a display, and one or more input devices. In various implementations, the display is integrated with one of the input devices as a touch-sensitive display. In some implementations, the method 500 is performed by processing logic, including hardware, firmware, software, or a combination thereof. In some implementations, the method 500 is performed by a processor executing code stored in a non-transitory computer-readable medium (e.g., a memory). Briefly, the method 500 includes obtaining first and second patient adherence expectation data, receiving first and second patient adherence data, and displaying first and second user interfaces including relational representations of patient adherence data and patient adherence expectation data.

The method 500 begins, at block 510, with the electronic device obtaining first patient adherence expectation data and second patient adherence expectation data, the first patient adherence expectation data indicative of a first set of actions and associated with a first patient account and the second patient adherence expectation data indicative of a second set of actions and associated with a second patient account. In various implementations, the first patient adherence expectation data and the second patient adherence expectation data are received via a network interface, e.g., from a secure cloud storage system. In various implementations, the first patient adherence expectation data and the second patient adherence expectation data are stored locally in non-transitory memory of the electronic device.

The first patient adherence expectation data is indicative of a first set of actions the first patient is expected to complete. The first set of actions can include a first set of activities the patient is expected to complete and/or a first a set of measurements the patient is expected to take. In various implementations, an action includes performing an activity, taking a measurement, or synching a device to receive a measurement from an external device. In various implementations, the first set of actions (for a first patient) is different from the second set of actions (for the second patient). In various implementations, the set of actions includes performing the same action multiple times a day.

In various implementations, the first patient adherence expectation data (and, in a similar manner, the second patient adherence expectation data) can be changed by a health manager interacting with the electronic device. In one embodiment, the electronic device detects, via one or more input devices, a request to edit the first patient adherence expectation data. For example, in FIG. 2O, the device detects a contact 299M at a location of the manage affordance 261E. In response to detecting the request to edit the first patient adherence expectation data, the device displays a manage edit user interface including options to edit the first patient adherence expectation data. For example, in FIG. 2I, the device displays a manage user interface 204E.

In various implementations, the options to edit the first patient adherence expectation data include an option to edit one or more of the first set of actions. For example, in FIG. 2P, the manage user interface 204E includes an edit item affordance 261L to edit the details of an activity included in the first set of actions. In various implementations, the options to edit one or more of the first set of actions includes an option to set an alert threshold associated with one or more of the first set of actions. For example, in FIG. 2Q, the manage user interface 204E includes an option to set an alert threshold for taking a multivitamin. In various implementations, the options to edit the patient adherence expectation data include an option to add one or more additional actions to the first set of actions. For example, in FIG. 2S, the manage user interface 204E includes an add item affordance 261K to add one or more activities to the set of actions. In various implementations, the options to add one or more additional actions to the first set of actions include an option to add a template of two or more different actions to the first set of actions. For example, in FIG. 2T, the manage user interface 204E includes an item menu 261S with options 261T to add item templates to the activity listing. Upon selection of an item template, two or more activities are added to the activity listing.

The method 500 continues, at block 520, with the electronic device receiving, from a first patient device associated with the first patient account, first patient adherence data indicative of actions completed by a first patient associated with the first patient account. In various implementations, the first patient adherence data is received via a network interface. The first patient adherence data can be received directly from the first patient device (over a network) or retrieved from a secure cloud storage system after being stored there by the first patient device. As noted above, in various implementations, the actions include activities performed by the patient and/or measurements taken by the patient. The actions can include, for example, taking a medication, performing a physical activity (such as walking or stretching), measuring a vital (such as a blood sugar level), providing a subjective (such as a pain level or a mood level), or taking a photograph (such as a photograph of a rash).

The method 500 continues, at block 530, with the electronic device receiving, from a second patient device associated with the second patient account, second patient adherence data indicative of actions completed by a second patient associated with the second patient account. In various implementations, the second patient adherence data is received via a network interface. The second patient adherence data can be received directly from the second patient device (over a network) or retrieved from a secure cloud storage system after being stored there by the second patient device.

The method 500 continues, at block 540, with the electronic device displaying a first user interface including a first relational representation of the first patient adherence data to the first patient adherence expectation data. For example, in FIG. 2N, the care card user interface 204B includes a number of relational representations of the first patient adherence data to the first patient adherence expectation data, including the activity indicia 261H, the daily percentage indicator 261I, and the activity adherence calendar 261J. Similarly, in FIG. 2V, the symptom tracker user interface 204C includes a number of relational representations of the first patient adherence data to the first patient adherence expectation data, including the measurement indicia 262C, the daily percentage indicator 262D, and the measurement adherence calendar 262E.

In various implementations, the first relational representation includes a representation of a percentage of the first set of actions associated with a date that are included in the actions completed by the first patient associated with the date. For example, in FIG. 2N, the daily percentage indicator 261I includes both a textual and graphical representation of a percentage of the first set of actions (in the form of a set of activities to be performed) associated with a particular date that have been completed by the patient. As another example, in FIG. 2V, the daily percentage indicator 262D includes both a textual and a graphical representation of a percentage of the first set of actions (in the form of a set of measurements to be taken) associated with a particular date that have been completed by the patient.

In various implementations, the first relational representation includes action indicia for each of the first set of actions associated with a date, wherein action indicia corresponding to actions completed by the first patient associated with the date are displayed in a first manner and other action indicia are displayed in a second manner different than the first manner. For example, in FIG. 2N, the activity indicia 261H include a separate indicia for each of the first set of actions associated with a date. Similarly, in FIG. 2V, the measurement indicia 262C include a separate indicia for each of the first set of actions associated with a date. The representation formed by the activity indicia 261H (and, similarly, the measurement indicia 262C) is relational by virtue of the different manners of display, in that completed actions are displayed differently than uncompleted actions. In various implementations, the first manner includes a completion indicator and the second manner does not include the completion indicator. In various implementations, the completion indicator is a shape fill. For example, in FIG. 2N, activity indicia 261H associated with completed activities include a filled shape and activity indicia 261H associated with uncompleted activities include an empty shape. Thus, the completion indicator is the inside of the shape which is present in activity indicia 261H associated with completed activities, but absent in activity indicia 261H associated with uncompleted activities. In various implementations, the completion indicator is a representation of a measurement. For example, in FIG. 2V, measurement indicia 262C associated with completed measurements include a value and measurement indicia 262C associated with uncompleted measurements include no value. Thus, the completion indicator is a measurement value which is present in measurement indicia 262C associated with completed measurements, but absent in measurement indicia 262C associated with uncompleted measurements.

In various implementations, the action indicia are organized into sets (e.g., by action to be repeated multiple times and/or action type (e.g., medications, physical activity, and other)). In various implementations, action indicia associated with one set are displayed in a different manner than action indicia associated with another set. For example, in FIG. 2N, the activity indicia 261H associated with taking a multivitamin is displayed in a different color than the activity indicia 261H associated with performing meditation. In various implementations, different sets of activity indicia 261H are displayed in a different color, size, shape, or font. Accordingly, in various implementations, a first set of the action indicia are displayed in a third manner and a second set of the action indicia is displayed are displayed in a fourth manner different than the third manner. In various implementations, the third manner includes a first color and the fourth manner includes a second color different than the first color. In various implementations, the third manner includes a first shape, size, or font and the fourth manner includes a second shape, size, or font different than the first shape, size, or font.

As mentioned above with respect to block 510, the first patient adherence expectation data can be changed by a health manager interacting with the electronic device. Similarly, the patient adherence data can be changed by a health manager. In various implementations, the electronic device detects a user input indicative of one or more additional actions completed by the first patient. For example, in FIG. 2N, the health manager device 120 detects the contact 299L at the location of one of the activity indicia 261H. In response to detecting the user input, the electronic device updates the first relational representation. For example, in FIG. 2O, the activity indicia 261H that was selected is filled and the daily percentage indicator 261I indicates an increased percentage.

The patient adherence data can also be changed by the patient by interacting with a patient device. For example, in FIG. 3A, the patient can touch one of the activity indicia 311D to indicate that an action has been completed. As another example, in FIG. 3B, the patient can input a value into one of the measurement indicia 321D to indicate that an action has been completed. At the health manager device, in various implementations, the electronic device receives, from the first patient device associated with the first patient account, updated first patient adherence data indicative of one or more additional actions completed by the first patient. In response to receiving the updated first patient adherence data, the electronic device updates the first relational representation.

The method continues, at block 550, with the electronic device displaying a second user interface including a second relational representation of the second patient adherence data to the second patent adherence expectation data. The second user interface can have the same features as the first user interface. For example, FIG. 2Z illustrates a care card user interface 204G for a second patient, similar to the care card user interface 204B for a first patient of FIG. 2N.

Figure 6:
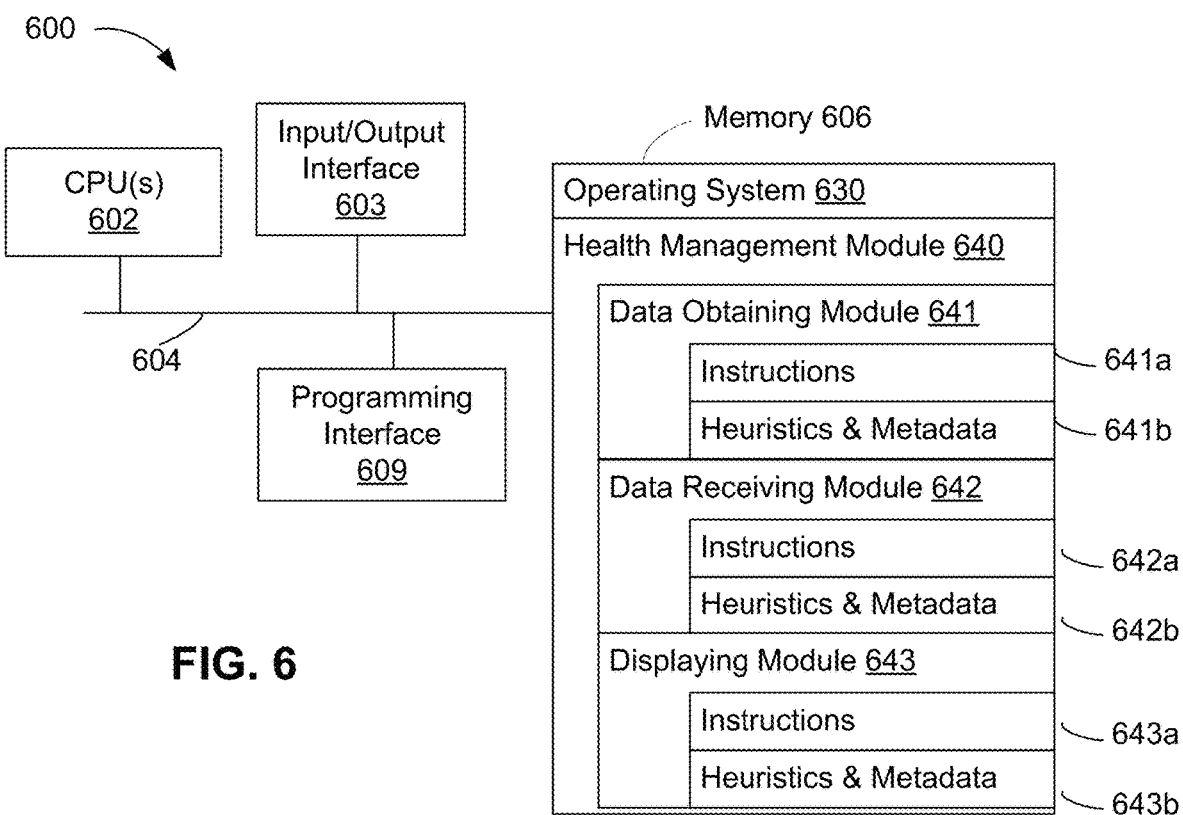
FIG. 6 is a block diagram of a computing device in accordance with some implementations.

FIG. 6 is a block diagram of a computing device 600 in accordance with some implementations. In some implementations, the computing device 600 corresponds to the at least a portion of the health manager device 120 of FIG. 1 and performs one or more of the functionalities described above with respect to the health manager device 120. While certain specific features are illustrated, those skilled in the art will appreciate from the present disclosure that various other features have not been illustrated for the sake of brevity, and so as not to obscure more pertinent aspects of the embodiments disclosed herein. To that end, as a non-limiting example, in some embodiments the computing device 600 includes one or more processing units (CPUs) 602 (e.g., processors), one or more input/output interfaces 603 (e.g., a network interface and/or a sensor interface), a memory 606, a programming interface 609, and one or more communication buses 604 for interconnecting these and various other components.

In some implementations, the communication buses 604 include circuitry that interconnects and controls communications between system components. The memory 606 includes high-speed random access memory, such as DRAM, SRAM, DDR RAM or other random access solid state memory devices; and, in some implementations, include non-volatile memory, such as one or more magnetic disk storage devices, optical disk storage devices, flash memory devices, or other non-volatile solid state storage devices. The memory 606 optionally includes one or more storage devices remotely located from the CPU(s) 602. The memory 606 comprises a non-transitory computer readable storage medium. Moreover, in some implementations, the memory 606 or the non-transitory computer readable storage medium of the memory 606 stores the following programs, modules and data structures, or a subset thereof including an optional operating system 630 and a health management module 640. In some implementations, one or more instructions are included in a combination of logic and non-transitory memory. The operating system 630 includes procedures for handling various basic system services and for performing hardware dependent tasks. In some implementations, the health management module 640 is configured to display information regarding one or more patients. To that end, the health management module 640 includes a data obtaining module 641, a data receiving module 642, and a displaying module 643.

In some implementations, the data obtaining module 641 is configured to obtain first patient display data indicating a first set of health metric types associated with a first patient account and second patient display data indicating a second set of health metric types associated with a second patient account. In some implementations, the data obtaining module 641 is configured to obtain first patient adherence expectation data and second patient adherence expectation data, the first patient adherence expectation data indicative of a first set of actions and associated with a first patient account and the second patient adherence expectation data indicative of a second set of actions and associated with a second patient account. To that end, the data obtaining module 641 includes a set of instructions 641a and heuristics and metadata 641b.

In some implementations, the data receiving module 642 is configured to receive, from a first patient device associated with the first patient account, first patient health data associated with the first patient account. In some implementations, the data receiving module 642 is configured to receive, from a second patient device associated with the second patient account, second patient health data associated with the second patient account. In some implementations, the data receiving module 642 is configured to receive, from a first patient device associated with the first patient account, first patient adherence data indicative of actions completed by a first patient associated with the first patient account. In some implementations, the data receiving module 642 is configured to receive, from a second patient device associated with the second patient account, second patient adherence data indicative of actions completed by a second patient associated with the second patient account. To that end, the data receiving module 642 includes a set of instructions 642a and heuristics and metadata 642b.

In some implementations, the displaying module 643 is configured to display a user interface including a first patient data region and a second patient data region, the first patient data region including representations of values for the first set of health metric types selected from the first patient health data and the second patient data region including representations of values for the second set of health metric types selected from the second patient health data. In some implementations, the displaying module 643 is configured to display a first user interface including a first relational representation of the first patient adherence data to the first patient adherence expectation data. In some implementations, the displaying module 643 is configured to display a second user interface including a second relational representation of second patient adherence data to the second patient adherence expectation data. To that end, the displaying module 643 includes a set of instructions 643a and heuristics and metadata 643b.

Although the health management module 640, the data obtaining module 641, the data receiving module 642, and the displaying module 643 are illustrated as residing on a single computing device 600, it should be understood that in other embodiments, any combination of the health management module 640, the data obtaining module 641, the data receiving module 642, and the displaying module 643 can reside in separate computing devices in various implementations. For example, in some implementations each of the health management module 640, the data obtaining module 641, the data receiving module 642, and the displaying module 643 reside on a separate computing device or in the cloud.

Moreover, FIG. 6 is intended more as functional description of the various features which are present in a particular implementation as opposed to a structural schematic of the embodiments described herein. As recognized by those of ordinary skill in the art, items shown separately could be combined and some items could be separated. For example, some functional modules shown separately in FIG. 6 could be implemented in a single module and the various functions of single functional blocks could be implemented by one or more functional blocks in various embodiments. The actual number of modules and the division of particular functions and how features are allocated among them will vary from one embodiment to another, and may depend in part on the particular combination of hardware, software and/or firmware chosen for a particular embodiment.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional sub-components to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed.

Some or all of the methods and tasks described herein may be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various functions disclosed herein may be embodied in such program instructions, although some or all of the disclosed functions may alternatively be implemented in application-specific circuitry (e.g., ASICs or FPGAs or GP-GPUs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various embodiments described above can be combined to provide further embodiments. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

The invention claimed is:

1. A method comprising:
at a heath manager device, associated with a health manager account, with one or more processors, non-transitory memory, a network interface, a display, and one or more input devices:
obtaining first patient display data indicating a first set of health metric types associated with a first patient account and second patient display data indicating a second set of health metric types associated with a second patient account;
receiving, via the network interface from a first patient device associated with the first patient account, first patient health data associated with the first patient account;
receiving, via the network interface from a second patient device associated with the second patient account, second patient health data associated with the second patient account;
displaying, on the display, a user interface including a first patient data region and a second patient data region, the first patient data region including a first set of health widgets that display values for the first set of health metric types selected from the first patient health data and the second patient data region including a second set of health widgets that display values for the second set of health metric types selected from the second patient health data;
detecting a user input at a location corresponding to the first set of health widgets;
in response to detecting the user input, shifting the first patient display area to display an edit affordance for modifying the first set of health widgets;
detecting a user selection of the edit affordance; and
in response to detecting the user selection of the edit affordance, displaying a widget edit user interface that allows changing the first set of health metric types.

2. The method of claim 1, wherein the first set of health metric types is different from the second set of health metric types.

3. The method of claim 1, wherein the first patient data region includes an alert indication that a value of the first patient health data exceeds an alert threshold.

4. The method of claim 1, wherein, responsive to a respective value for the first set of health metric types exceeding a first alert threshold, the respective value is displayed in a different manner than another value for the first set of health metric types.

5. The method of claim 4, wherein, responsive to a respective value for the second set of health metric types exceeding a second alert threshold, the respective value is displayed in a different manner than another value for the second set of health metric types, wherein the second alert threshold is different than the first alert threshold.

6. The method of claim 1, wherein the user interface includes a plurality of patient data regions including the first patient data region and the second patient data region, further comprising:
detecting, via the one or more input devices, selection of a filter affordance displayed in the user interface;

in response to detecting selection of the filter affordance, displaying, on the display in the user interface, options to select one or more filter criteria;

detecting, via the one or more input devices, selection of one or more filter criteria; and in response to detecting selection of the one or more filter criteria, ceasing to display those of the plurality of patient data regions associated with patient accounts failing to meet the filter criteria.

7. The method of claim 6, wherein the one or more filter criteria includes at least one of a patient categorization criterion, a health manager criterion, an alert-presence criterion, or a search term matching criterion.

8. The method of claim 1, further comprising:
detecting, via the one or more input devices, a request to edit the first patient display data; and
in response to detecting the request to edit the first patient display data, displaying a widget edit user interface including options to edit the first patient display data.

9. The method of claim 8, wherein the options to edit the first patient display data include an option to display a list of selectable health metric types.

10. The method of claim 8, wherein the options to edit the first patient display data include an option to set an alert threshold associated with one of the first set of health metric types.

11. The method of claim 1, further comprising:
detecting a contact at a location corresponding to the first patient data region; and
in response to detecting the contact, displaying an affordance to view adherence to a first treatment plan associated with the first patent account.

12. The method of claim 11, further comprising:
detecting a user selection of the affordance; and
in response to detecting the user selection of the affordance, displaying:
a daily activity adherence region that indicates adherence to activities specified by the first treatment plan for a particular day; and
a historical activity adherence region that indicates adherence to the treatment plan over a plurality of days.

13. The method of claim 12, wherein the daily activity adherence region displays a plurality of activity indicia corresponding to activities specified by the first treatment plan for that particular day;
wherein a first subset of the plurality of activity indicia corresponding to completed activities is displayed with a first visual characteristic; and
wherein a second subset of the plurality of activity indicia corresponding to incomplete activities is displayed with a second visual characteristic that is different from the first visual characteristic.

14. A non-transitory computer-readable medium having instructions encoded thereon that, when executed by one or more processors of an electronic device, cause the electronic device to perform a method comprising:
obtaining first patient display data indicating a first set of health metric types associated with a first patient account and second patient display data indicating a second set of health metric types associated with a second patient account;
receiving, via the network interface from a first patient device associated with the first patient account, first patient health data associated with the first patient account;
receiving, via the network interface from a second patient device associated with the second patient account, second patient health data associated with the second patient account;
displaying, on the display, a user interface including a first patient data region and a second patient data region, the first patient data region including a first set of health widgets that display values for the first set of health metric types selected from the first patient health data and the second patient data region including a second set of health widgets that display values for the second set of health metric types selected from the second patient health data;
detecting a user input at a location corresponding to the first set of health widgets;
in response to detecting the user input, shifting the first patient display area to display an edit affordance for modifying the first set of health widgets;
detecting a user selection of the edit affordance; and
in response to detecting the user selection of the edit affordance, displaying a widget edit user interface that allows changing the first set of health metric types.

15. The non-transitory computer-readable medium of claim 14, wherein the first set of health metric types is different from the second set of health metric types.

16. The non-transitory computer-readable medium of claim 14, wherein the first patient data region includes an alert indication that a value of the first patient health data exceeds an alert threshold.

17. The non-transitory computer-readable medium of claim 14, wherein, responsive to a respective value for the first set of health metric types exceeding a first alert threshold, the respective value is displayed in a different manner than another value for the first set of health metric types.

18. The non-transitory computer-readable medium of claim 17, wherein, responsive to a respective value for the second set of health metric types exceeding a second alert threshold, the respective value is displayed in a different manner than another value for the second set of health metric types, wherein the second alert threshold is different than the first alert threshold.

19. The non-transitory computer-readable medium of claim 14, wherein the user interface includes a plurality of patient data regions including the first patient data region and the second patient data region, the method further comprising:
detecting, via the one or more input devices, selection of a filter affordance displayed in the user interface;
in response to detecting selection of the filter affordance, displaying, on the display in the user interface, options to select one or more filter criteria;
detecting, via the one or more input devices, selection of one or more filter criteria; and
in response to detecting selection of the one or more filter criteria, ceasing to display those of the plurality of patient data regions associated with patient accounts failing to meet the filter criteria.

20. The non-transitory computer-readable medium of claim 19, wherein the one or more filter criteria includes at least one of a patient categorization criterion, a health manager criterion, an alert-presence criterion, or a search term matching criterion.

21. The non-transitory computer-readable medium of claim 14, the method further comprising:
detecting, via the one or more input devices, a request to edit the first patient display data; and in response to detecting the request to edit the first patient display data, displaying a widget edit user interface including options to edit the first patient display data.

22. The non-transitory computer-readable medium of claim 21, wherein the options to edit the first patient display data include an option to display a list of selectable health metric types.

23. A health manager device comprising:
a display;
a network interface;
one or more input devices;
a non-transitory memory; and
one or more processors configured to:
  obtain first patient display data indicating a first set of health metric types associated with a first patient account and second patient display data indicating a second set of health metric types associated with a second patient account;
  receive, via the network interface from a first patient device associated with the first patient account, first patient health data associated with the first patient account;
  receive, via the network interface from a second patient device associated with the second patient account, second patient health data associated with the second patient account;
  display, on the display, a user interface including a first patient data region and a second patient data region, the first patient data region including a first set of health widgets that display values for the first set of health metric types selected from the first patient health data and the second patient data region including a second set of health widgets that display values for the second set of health metric types selected from the second patient health data;
  detect, via the one or more input devices, a user input at a location corresponding to the first set of health widgets;
  in response to detecting the user input, shift the first patient display area to display an edit affordance for modifying the first set of health widgets;
  detect, via the one or more input devices, a user selection of the edit affordance; and
  in response to detecting the user selection of the edit affordance, display, on the display, a widget edit user interface that allows changing the first set of health metric types.

* * * * *

UNITED STATES PATENT AND TRADEMARK OFFICE
CERTIFICATE OF CORRECTION

PATENT NO. : 10,984,898 B2
APPLICATION NO. : 15/978126
DATED : April 20, 2021
INVENTOR(S) : Divya Nag et al.

Page 1 of 1

It is certified that error appears in the above-identified patent and that said Letters Patent is hereby corrected as shown below:

In the Claims

In Column 22, Line 9, Claim 1, delete "heath" and insert -- health --, therefor.

In Column 23, Line 33, Claim 11, delete "patent" and insert -- patient --, therefor.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*